United States Patent
Shelton, IV et al.

(10) Patent No.: US 11,601,232 B2
(45) Date of Patent: Mar. 7, 2023

(54) REDUNDANT COMMUNICATION CHANNELS AND PROCESSING OF IMAGING FEEDS

(71) Applicant: Cilag GmbH International, Zug (CH)

(72) Inventors: Frederick E. Shelton, IV, Hillsboro, OH (US); Bernhard Adolf Fuerst, Sunnyvale, CA (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/384,265

(22) Filed: Jul. 23, 2021

(65) Prior Publication Data

US 2023/0025827 A1    Jan. 26, 2023

Related U.S. Application Data

(60) Provisional application No. 63/224,813, filed on Jul. 22, 2021.

(51) Int. Cl.
*H04N 7/15*      (2006.01)
*H04L 1/22*      (2006.01)
(Continued)

(52) U.S. Cl.
CPC ............... *H04L 1/22* (2013.01); *H04L 65/80* (2013.01); *H04N 7/15* (2013.01); *A61B 8/06* (2013.01)

(58) Field of Classification Search
CPC .............. H04L 1/22; H04L 29/06; H04N 7/15
(Continued)

(56) References Cited

U.S. PATENT DOCUMENTS 6,766,373 B1    7/2004    Beadle et al.
9,011,427 B2    4/2015    Price et al.
(Continued)

FOREIGN PATENT DOCUMENTS

WO    WO-2013174327 A1 * 11/2013 ........... H04L 1/0017
WO    WO-2017089479 A1 * 6/2017 ........... A61B 5/0071
(Continued)

OTHER PUBLICATIONS

Document ID JP 2017504019 A5 Date Published Dec. 28, 2017.*
(Continued)

*Primary Examiner* — Melur Ramakrishnaiah
(74) *Attorney, Agent, or Firm* — Condo Roccia Koptiw LLP

(57) ABSTRACT

A computing system may use redundant communication pathways for communicating surgical imaging feed(s). The computing system may obtain multiple surgical video streams via multiple pathways. The multiple surgical video streams may include copies of the same video. The surgical video streams may be obtained, for example, from the same intra-body imaging feed, such as intra-body visual light feed. For example, a first video stream may be obtained via a communication pathway, and a second video stream may be obtained via another communication pathway. The computing system may display or send a surgical video stream for display. The computing system may whether the video stream being displayed has encountered any issues. Upon detecting an issue with the video stream being displayed, the computing system may display or send another obtained surgical video stream for display.

16 Claims, 20 Drawing Sheets

(51) Int. Cl.
*H04L 65/80* (2022.01)
*A61B 8/06* (2006.01)

(58) Field of Classification Search
USPC .......................................... 348/14.01–14.16
See application file for complete search history.

(56) References Cited

U.S. PATENT DOCUMENTS

| | | |
|---|---|---|
| 9,283,054 B2 | 3/2016 | Morgan et al. |
| 9,345,481 B2 | 5/2016 | Hall et al. |
| 2002/0000464 A1 | 1/2002 | Ramberg et al. |
| 2013/0149967 A1* | 6/2013 | Ma ........................... H04B 1/74 |
| | | 455/41.2 |
| 2014/0160259 A1 | 6/2014 | Blanquart et al. |
| 2014/0160260 A1 | 6/2014 | Blanquart et al. |
| 2014/0263552 A1 | 9/2014 | Hall et al. |
| 2014/0267655 A1 | 9/2014 | Richardson et al. |
| 2015/0128274 A1 | 5/2015 | Giokas et al. |
| 2017/0296213 A1 | 10/2017 | Swensgard et al. |
| 2018/0344308 A1 | 12/2018 | Nawana et al. |
| 2018/0360452 A1 | 12/2018 | Shelton, IV et al. |
| 2019/0191963 A1 | 6/2019 | Kuhn et al. |
| 2019/0200844 A1 | 7/2019 | Shelton, IV et al. |
| 2019/0200906 A1 | 7/2019 | Shelton, IV et al. |
| 2019/0200980 A1 | 7/2019 | Shelton, IV et al. |
| 2019/0200988 A1 | 7/2019 | Shelton, IV |
| 2019/0201033 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201115 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201129 A1 | 7/2019 | Shelton, IV et al. |
| 2019/0201137 A1 | 7/2019 | Shelton, IV et al. |
| 2019/0201140 A1 | 7/2019 | Yates et al. |
| 2019/0204201 A1 | 7/2019 | Shelton, IV et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206556 A1 | 7/2019 | Shelton, IV et al. |
| 2019/0206562 A1 | 7/2019 | Shelton, IV et al. |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207911 A1 | 7/2019 | Wiener et al. |
| 2020/0244734 A1* | 7/2020 | Mendiola ................ H04L 45/24 |
| 2021/0290046 A1* | 9/2021 | Nazareth ............ H04N 5/23293 |
| 2022/0104713 A1 | 4/2022 | Shelton, IV et al. |
| 2022/0104896 A1 | 4/2022 | Shelton, IV et al. |
| 2022/0233119 A1 | 7/2022 | Shelton, IV et al. |
| 2022/0233135 A1 | 7/2022 | Shelton, IV et al. |
| 2022/0233136 A1 | 7/2022 | Shelton, IV et al. |
| 2022/0233151 A1 | 7/2022 | Shelton, IV et al. |
| 2022/0233191 A1 | 7/2022 | Shelton, IV et al. |
| 2022/0233252 A1 | 7/2022 | Shelton, IV et al. |
| 2022/0233254 A1 | 7/2022 | Shelton, IV et al. |
| 2022/0238216 A1 | 7/2022 | Shelton, IV et al. |
| 2022/0240869 A1 | 8/2022 | Shelton, IV et al. |
| 2022/0241028 A1 | 8/2022 | Shelton, IV et al. |
| 2022/0241474 A1 | 8/2022 | Shelton, IV et al. |

FOREIGN PATENT DOCUMENTS

| | | |
|---|---|---|
| WO | 2019-119130 A1 | 6/2019 |
| WO | WO-2021048326 A1 * | 3/2021 |

OTHER PUBLICATIONS

U.S. Appl. No. 17/384,354, filed Jul. 23, 2021, Shelton, IV et al.
U.S. Appl. No. 17/384,453, filed Jul. 23, 2021, Shelton, IV et al.
U.S. Appl. No. 17/384,455, filed Jul. 23, 2021, Shelton, IV et al.
U.S. Appl. No. 17/384,457, filed Jul. 23, 2021, Shelton, IV et al.
U.S. Appl. No. 17/384,508, filed Jul. 23, 2021, Shelton, IV et al.
U.S. Appl. No. 17/384,553, filed Jul. 23, 2021, Shelton, IV et al.
U.S. Appl. No. 17/384,128, filed Oct. 15, 2020, Shelton, IV et al.
U.S. Appl. No. 17/384,142, filed Jul. 23, 2021, Shelton, IV et al.
U.S. Appl. No. 17/384,151, filed Jul. 23, 2021, Shelton, IV et al.
U.S. Appl. No. 17/384,164, filed Jul. 23, 2021, Shelton, IV et al.
U.S. Appl. No. 17/384,270, filed Jul. 23, 2021, Shelton, IV et al.
U.S. Appl. No. 17/384,274, filed Jul. 23, 2021, Shelton, IV et al.
U.S. Appl. No. 17/384,337, filed Jul. 23, 2021, Shelton, IV et al.
U.S. Appl. No. 17/384,348, filed Jul. 23, 2021, Shelton, IV et al.
U.S. Appl. No. 62/611,341, filed Dec. 28, 2017, Shelton, IV et al.
Jagannath Swathi, et al., "An Analysis of Speech as a Modality for Activity Recognition during Complex Medical Teamwork", Int Conf Pervasive Comput Technol Healthc. May 2018, 23 pages.

* cited by examiner

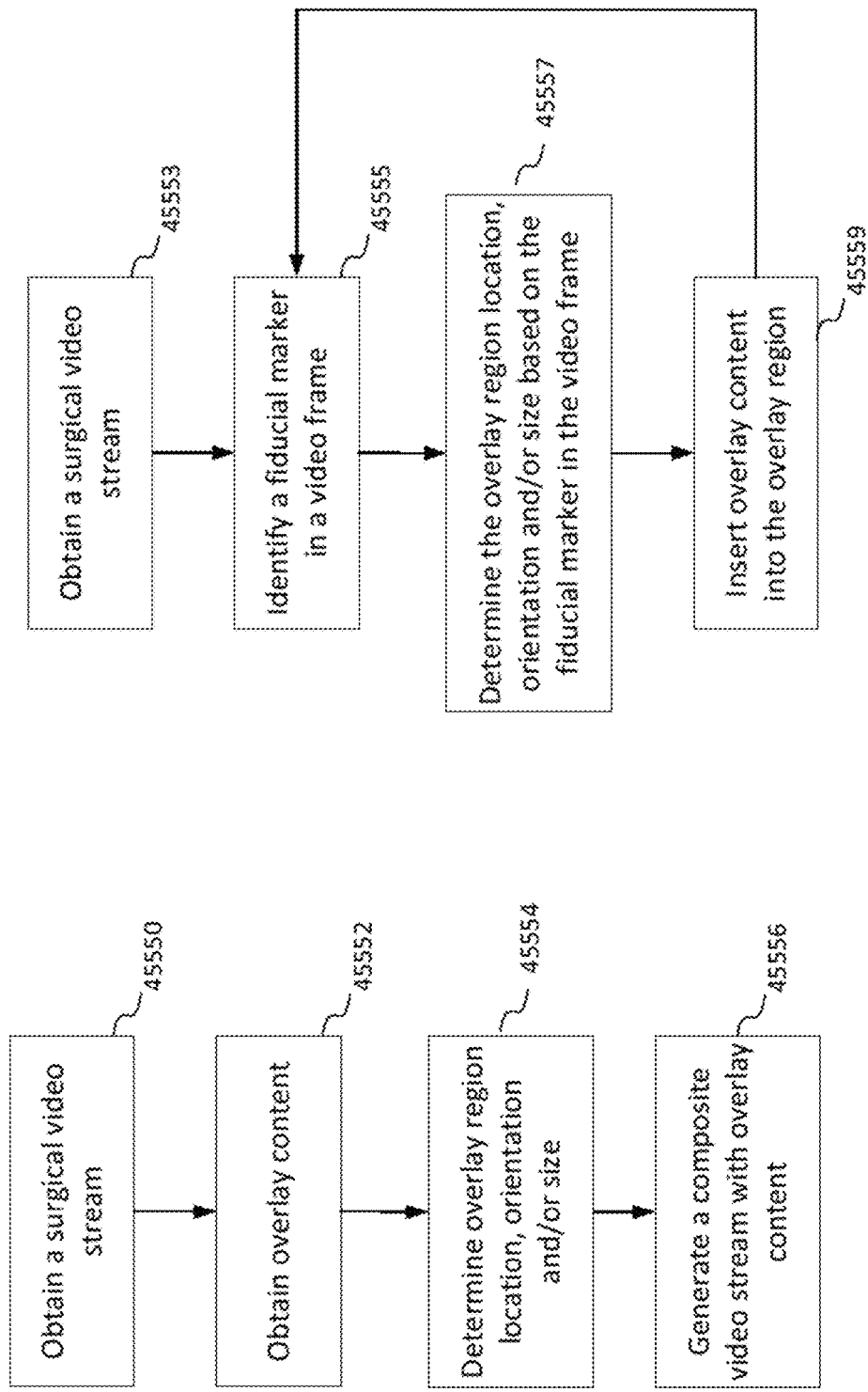

REDUNDANT COMMUNICATION CHANNELS AND PROCESSING OF IMAGING FEEDS

CROSS-REFERENCE TO RELATED APPLICATIONS

This application claims the benefit of Provisional U.S. Patent Application No. 63/224,813, filed Jul. 22, 2021, the disclosure of which is incorporated herein by reference in its entirety.

This application is related to the following, filed contemporaneously, the contents of each of which are incorporated by reference herein:
- U.S. patent application Ser. No. 17/384,274, filed Jul. 23, 2021, entitled METHOD OF SURGICAL SYSTEM POWER MANAGEMENT, COMMUNICATION, PROCESSING, STORAGE AND DISPLAY; and
- U.S. patent application Ser. No. 17/384,270, filed Jul. 23, 2021, entitled COOPERATIVE COMPOSITE VIDEO STREAMS LAYERED ONTO THE SURGICAL SITE AND INSTRUMENTS.

BACKGROUND

Surgical procedures are typically performed in surgical operating theaters or rooms in a healthcare facility such as, for example, a hospital. Various surgical devices and systems are utilized in performance of a surgical procedure. In the digital and in formation age, medical systems and facilities are often slower to implement systems or procedures utilizing newer and improved technologies due to patient safety and a general desire for maintaining traditional practices. It is desirable to improve the delivery and processing of surgical video feeds, such as an intraoperative video feed captured by a laparoscopic scope.

SUMMARY

A computing system may use redundant communication pathways for communicating surgical imaging feed(s). The computing system may obtain multiple surgical video streams via multiple pathways. The multiple surgical video streams may include different video feeds and/or copies of the same video feed. The surgical video streams may be obtained, for example, from the same intra-body imaging feed, such as an intra-body visual light feed. For example, a first video stream may be obtained via a communication pathway, and a second video stream may be obtained via another communication pathway. The computing system may display or send a surgical video stream for display. The computing system may determine whether the video stream being displayed has encountered any issues. Upon detecting an issue with the video stream being displayed, the computing system may display another obtained surgical video stream or send another obtained surgical video stream for display. For example, a primary video stream may be displayed initially. Upon detecting an issue associated with the primary video, a secondary video stream may be displayed.

In examples, the computing system may use redundant processing paths for processing surgical imaging feed(s). The computing system may obtain a source surgical imaging stream and may process the source imaging stream using multiple processing modules. For example, at least some processing modules may process the surgical imaging stream in parallel. The computing system may determine whether any issues have been encountered at the processing modules. If no issue has been found, the processed surgical imaging streams may be merged for display. Upon detecting an issue associated with a processing module, the computing system may select a surgical imaging stream unaffected by the detected issue for display. For example, a surgical imaging stream that has not been processed by the processing module associated with the detected issue may be selected for display.

A computing system may generate a composite video stream from multiple input feeds. The computing system may obtain a surgical video stream and overlay content associated with a surgical procedure onto the surgical video stream. For example, the overlay content may be obtained from a secondary video feed or a portion of a secondary video feed. The computing system may determine the overlay region location, size and/or orientation for overlaying the overlay content by analyzing the content of surgical video stream. For example, based on the content of a frame of the surgical video stream, the computing system may determine an overlay region location in the frame for overlaying the overlay content. Based on the content of a subsequent frame of the surgical video stream, the computing system may determine another overlay region location in the subsequent frame for overlaying the overlay content. The composite video stream may be generated based on the overlay region locations determined for different frames of the surgical video stream.

The computing system may determine the overlay region location, size and/or orientation for overlaying the overlay content based on one or more fiducial marker(s) captured in the surgical video stream. For example, the computing system may identify the fiducial marker in the video frames of the surgical video stream and determine the respective location, size, and/or orientation of the fiducial marker(s) in respective video frames. For a given video frame, or a group of video frames, the computing system may determine the size, location and/or orientation of the overlay region based on the location, size and/or orientation of the fiducial marker captured therein.

BRIEF DESCRIPTION OF THE DRAWINGS

FIG. 18A illustrates an example process for generating a composite surgical video stream from multiple input feeds.

FIG. 18B shows an example process for generating a composite surgical video stream using a fiducial marker.

DETAILED DESCRIPTION

Applicant of the present application owns the following U.S. Patent Applications, each of which is herein incorporated by reference in its entirety:

U.S. patent application Ser. No. 15/940,654, entitled SURGICAL HUB SITUATIONAL AWARENESS, filed Mar. 29, 2018;

U.S. patent application Ser. No. 15/940,742, entitled DUAL CMOS ARRAY IMAGING, filed Mar. 29, 2018;

U.S. patent application Ser. No. 17/062,521, entitled TIERED-ACCESS SURGICAL VISUALIZATION SYSTEM, filed Oct. 2, 2020;

U.S. patent application Ser. No. 17/062,530, entitled SURGICAL HUB HAVING VARIABLE INTERCONNECTIVITY CAPABILITIES, filed Oct. 2, 2020;

U.S. patent application Ser. No. 17/062,512, entitled TIERED SYSTEM DISPLAY CONTROL BASED ON CAPACITY AND USER OPERATION, filed Oct. 2, 2020;

U.S. patent application Ser. No. 17/062,508, entitled COOPERATIVE SURGICAL DISPLAYS, filed Oct. 2, 2020;

U.S. patent application Ser. No. 17/062,509, entitled INTERACTIVE INFORMATION OVERLAY ON MULTIPLE SURGICAL DISPLAYS, filed Oct. 2, 2020;

U.S. patent application Ser. No. 17/062,507, entitled COMMUNICATION CONTROL FOR A SURGEON CONTROLLED SECONDARY DISPLAY AND PRIMARY DISPLAY, filed Oct. 2, 2020;

U.S. patent application Ser. No. 17/062,513, entitled SITUATIONAL AWARENESS OF INSTRUMENTS LOCATION AND INDIVIDUALIZATION OF USERS TO CONTROL DISPLAYS, filed Oct. 2, 2020;

U.S. patent application Ser. No. 17/062,517, entitled SHARED SITUATIONAL AWARENESS OF THE DEVICE ACTUATOR ACTIVITY TO PRIORITIZE CERTAIN ASPECTS OF DISPLAYED INFORMATION, filed Oct. 2, 2020;

U.S. patent application Ser. No. 17/062,520, entitled MONITORING OF USER VISUAL GAZE TO CONTROL WHICH DISPLAY SYSTEM DISPLAYS THE PRIMARY INFORMATION, filed Oct. 2, 2020;

U.S. patent application Ser. No. 17/062,519, entitled RECONFIGURATION OF DISPLAY SHARING, filed Oct. 2, 220; and U.S. patent application Ser. No. 17/062,516, entitled CONTROL OF A DISPLAY OUTSIDE THE STERILE FIELD FROM A DEVICE WITHIN THE STERILE FIELD, filed Oct. 2, 2020.

Figure 1A:
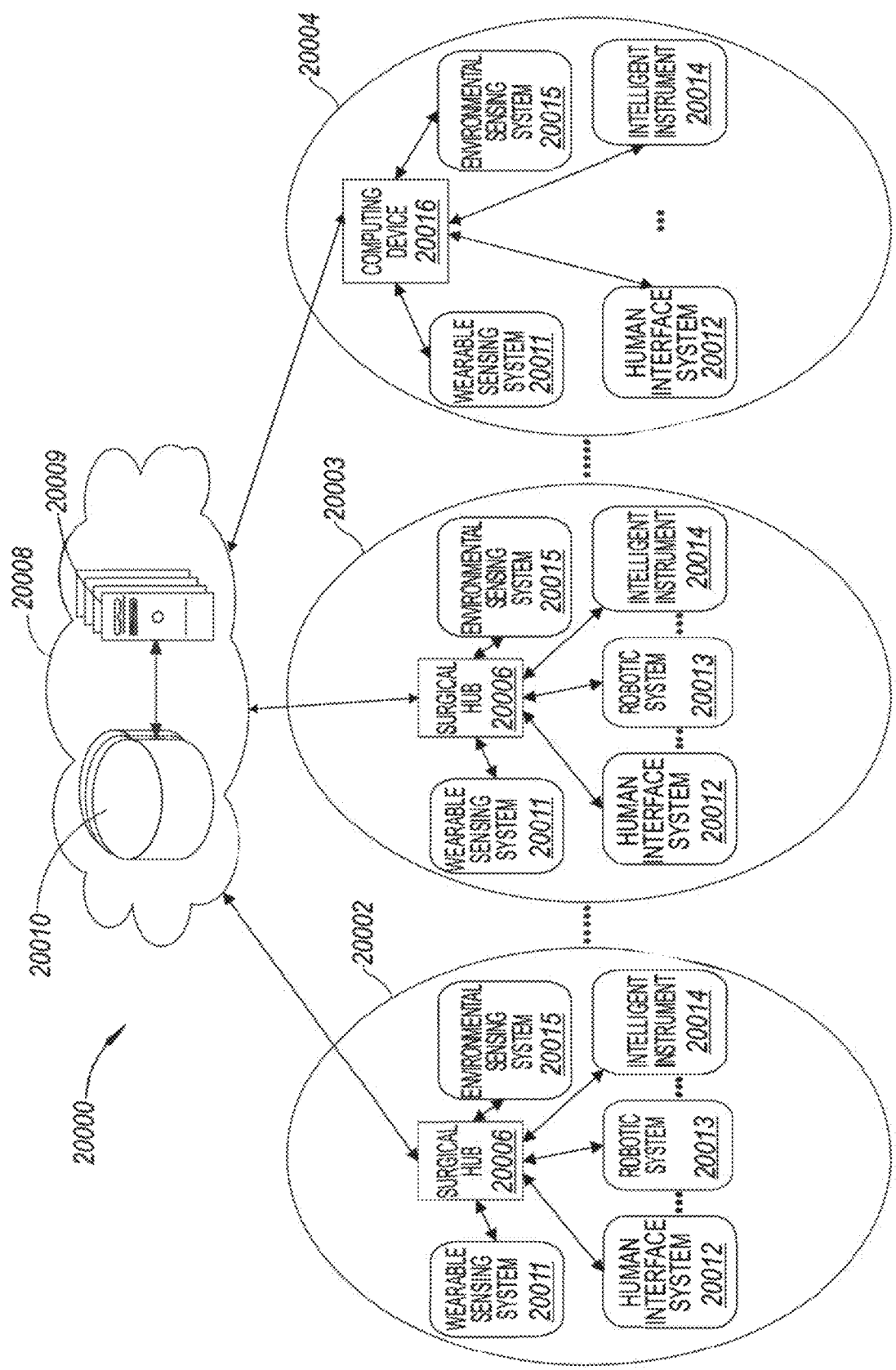
FIG. 1A is a block diagram of a computer-implemented surgical system.

FIG. 1A is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 20009 via an internet service provider's cable/FIOS networking node. In an example, a patient sensing system may be in direct communication with a remote server 20009. The surgical system 20002 and/or a component therein may communicate with the remote servers 2000) via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1A. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 1B:
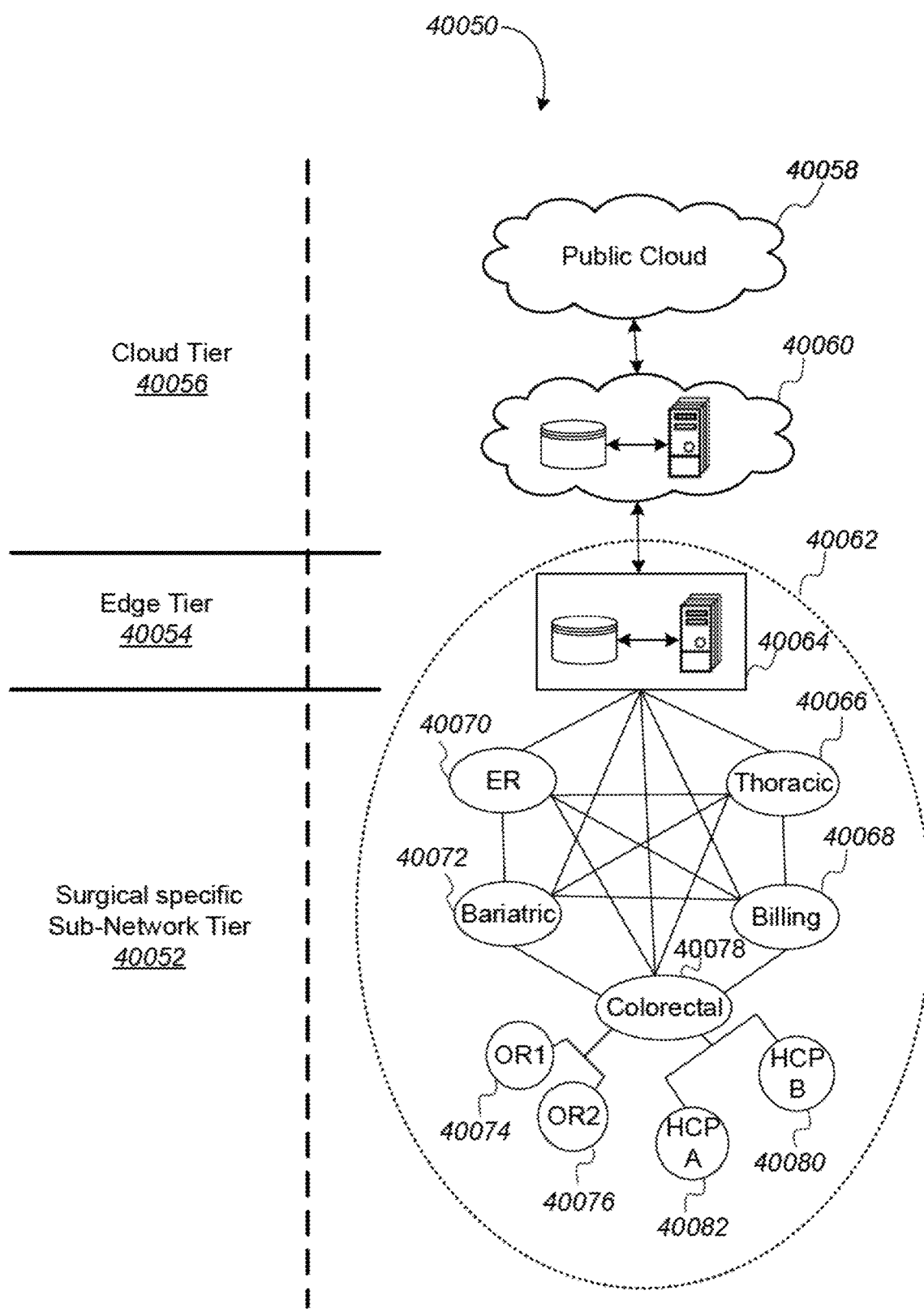
FIG. 1B is a block diagram of a computer-implemented multi-tier surgical system.

FIG. 1B is a block diagram of a computer-implemented multi-tier surgical system. As illustrated in FIG. 1B, a computer-implemented multi-tier surgical system 40050 may include multiple tiers of systems, such as a surgical specific sub-network tier system 4052, an edge tier system 40054 that is associated with the surgical specific sub-network tier system 40052, and a cloud tier system 40056.

A surgical specific sub-network tier system 40052 may include a plurality of inter-connected surgical sub-systems. For example, the surgical sub-systems may be grouped by the type of surgical procedures and/or other departments in a medical facility or a hospital. For example, a medical facility or a hospital may include a plurality of surgical procedure specific departments, such as an emergency room (ER) department 40070, colorectal department 40078, bariatric department 40072, thoracic department 40066, and billing department 40068. Each of the surgical procedure specific departments may include one or more surgical sub-systems associated with an operating room (OR) and/or a healthcare care professional (HCP). For example, the colorectal department 40078 may include a set of surgical hubs (e.g., surgical hub 20006 as described in FIG. 1A). The surgical hubs may be designated for a respective HCP, such as HCP A, 40082 and HCP B, 40080. In an example, the colorectal department may include a group of surgical hubs that may be located in respective ORs, such as OR 1, 40074 and OR 2, 40076. The medical facility or the hospital may also include a billing department subsystem 40068. The billing department subsystem 40068 may store and/or manage billing data associated with a respective department, such as the ER department 40070, colorectal department 40078, bariatric department 40072, and/or thoracic department 40066.

An edge tier system 40054 may be associated with a medical facility or a hospital and may include one or more edge computing systems 40064, for example. An edge computing system 40064 may include a storage sub-system and a server sub-system. In an example, the edge computing system comprising an edge server and/or a storage unit may provide additional processing and/or storage services to a surgical hub that is part of one of the departmental ORs (e.g., OR1 and OR2 of the colorectal department).

The surgical specific sub-network tier system 40052 and the edge tier system 40054 may be located within a Health Insurance Portability and Accountability Act (HIPAA) boundary 40062. The surgical specific sub-network system 40052 and the edge tier system 40054 may be connected to the same local data network. The local data network may be a local data network of a medical facility or a hospital. The local data network may be within the HIPAA boundary. Because the surgical specific sub-network tier system 40052 and the edge tier system 40054 are located within the HIPAA boundary 40062, patient data between an edge computing system 40064 and a device located within one of the entities of the surgical specific sub-network tier system 40052 may flow without redaction and/or encryption. For example, patient data between an edge computing system 4006- and a surgical hub located in OR1 40074 of the colorectal department 40078 may flow without redaction and/or encryption.

The cloud tier system 40056 may include an enterprise cloud system 40060 and a public cloud system 40058. For example, the enterprise cloud system 40060 may be a cloud computing system 20008 that includes a remote cloud server sub-system and/or a remote cloud storage subsystem, as described in FIG. 1A. The enterprise cloud system 40060 may be managed by an organization, such as a private company. The enterprise cloud system 40060 may be in communication with one or more entities (e.g., edge computing systems 40064, surgical hubs located in ORs (e.g., OR1 40074) of the various departments (e.g., colorectal department 40078)) that are located within the HIPAA boundary 40062.

The public cloud system 40058 may be operated by a cloud computing service provider. For example, the cloud computing service provider may provide storage services and/or computing services to a plurality of enterprise cloud systems (e.g., enterprise cloud system 40060).

Figure 1C:
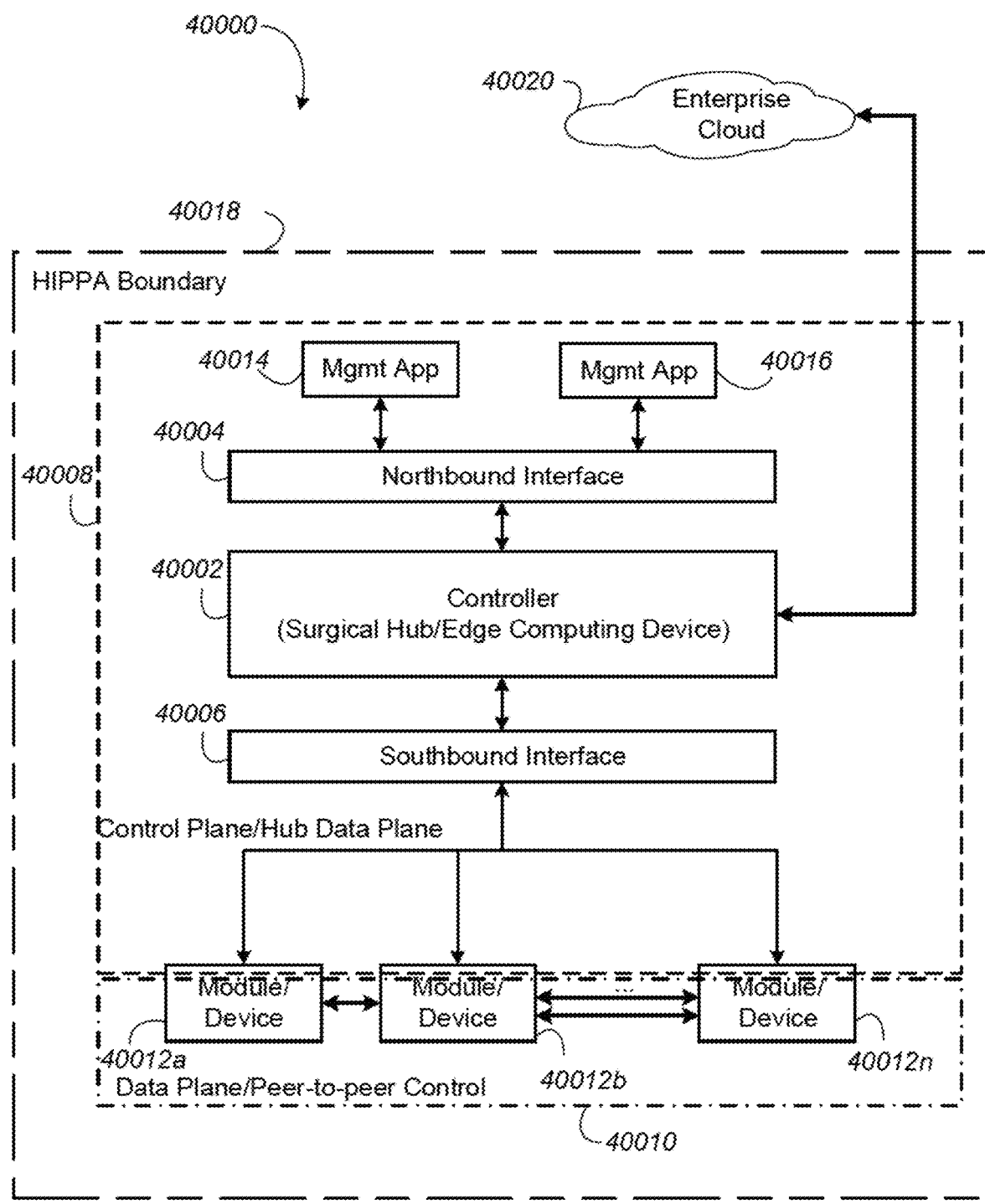
FIG. 1C is a logical diagram illustrating control plane and data plane of a surgical system.

FIG. 1C is a logical block diagram 40000 illustrating various communication planes in a surgical system. As illustrated in FIG. 1C, the communication planes between a controller 40002 and management applications 40014 and 40016 on one side and, the system modules and/or modular devices 40012a through 40012n on the other side, may use control plane 40008 and data plane 40010. In an example, in addition to the control plane 40008, a data plane may also exist between the system modules and/or modular devices 40012a through 40012n and the surgical hub. The data plane 40010 may provide data plane paths (e.g., redundant data plane paths) between the system modules and/or the modular devices 40012a through 40012n that are associated with one or more surgical hubs. A surgical hub or one of the surgical hubs (e.g., in case of a plurality of surgical hubs present in an operating room) may act as a controller 40002. In an example, the controller 40002 may be an edge computing system that may reside within a Health Insurance Portability and Accountability Act (HIPAA) boundary where the surgical system is located, for example, as illustrated in FIG. 1B. The controller 40002 may be in communication with an enterprise cloud system 40020. As illustrated in FIG. 1C, the enterprise cloud system 40020 may be located outside the HIPAA boundary 40018. Accordingly, the patient data flowing to and/or from the enterprise cloud system 40020 may be redacted and/or encrypted.

The controller 40002 may be configured to provide a northbound interface 40004 and a southbound interface 40006. The northbound interface 40004 may be used for providing a control plane 40008. The control plane 40008 may include one or more management applications 40014 and 40016 that may enable a user to configure and/or manage system modules and/or modular devices modular devices 40012a through 40012n associated with a surgical system. The management applications 40014 and 40016 may be used to obtain status of various system modules and/or the modular devices 40012a through 40012n.

The management applications 40014 and 40016 using the control plane may interact with the controller 40002, for example, using a set of application programming interface (API) calls. The management applications 40014 and 40016 may interact with the controller 40002 via a management protocol or an application layer protocol to configure and/or monitor the status of a system module and/or a modular device. The management protocols or the application layer protocols used to monitor the status and/or configure a system module or a modular device associated with a surgical system may include the simple network management protocol (SNMP), TELNET protocol, secure shell (SSH) protocol, network configuration protocol (NETCONF), etc.

SNMP or a similar protocol may be used to collect status information and/or send configuration related data (e.g., configuration related control programs) associated with system modules and/or modular devices to the controller. SNMP or a similar protocol may collect information by selecting devices associated with a surgical system from a central network management console using messages (e.g., SNMP messages). The messages may be sent and/or received at fixed or random intervals. The messages may include Get messages and Set messages. The Get messages or messages similar to the Get messages may be used for obtaining information from a system module or a modular device associated with a surgical system. The Set message or messages similar to the Set message may be used for changing a configuration associated with a system module or a modular device associated with a surgical system.

For example, the Get messages or similar messages may include the SNMP messages GetRequest, GetNextRequest, or GetBulkRequest. The Set messages may include SNMP SetRequest message. The GetRequest, GetNextRequest, GetBulkRequest messages or similar messages may be used by a configuration manager (e.g., an SNMP manager) running on the controller 40002. The configuration manager may be in communication with a communication agent (e.g., an SNMP agent) that may be a part of a system module and/or a modular device in a surgical system. The SNMP message SetRequest message or similar may be used by the communication manager on the controller 40002 to set the value of a parameter or an object instance in the communication agent on a system module and/or a modular device of a surgical system. In an example, SNMP modules, for example, may be used to establish communication path between system modules and/or modular devices associated with a surgical system.

Based on the query or configuration related messages received from a management application, such as management applications 40014 and 40016, the controller 40002 may generate configuration queries and/or configuration data for querying or configuring the system modules and/or the modular devices associated with the surgical hub or the surgical system. A surgical hub (e.g., the surgical hub 20006 shown in FIG. 1A) or an edge computing system (e.g., the edge computing system 40064 shown in FIG. 1B) may manage and/or control various system modules and/or modular devices 40012a through 40012n associated with a surgical system. For example, the northbound interface 40004 of the controller 40002 may be used for changing control interactions between one or more modules associated and/or devices associated with a surgical system. In an example, the controller 40002 may be used for establishing one or more communication data paths between a plurality of modules and/or devices associated with a surgical system. The controller 40002 may use its southbound interface 40006 to send the control programs comprising queries and/or configuration changes to the system modules and/or the modular devices of the surgical system.

The system modules and/or the modular devices 40012a through 40012n of a surgical system, or the communication agents that may be a part of the system modules and/or the modular devices, may send notification messages or traps to the controller 40002. The controller may forward the notification messages or traps via its northbound interface 40004 to the management application 40014 and 40016 for displaying on a display. In an example, the controller 40002 may send the notification to other system modules and/or modular devices 44012a through 40012n that are part of the surgical system.

The system modules and/or the modular devices 40012a through 40012n of a surgical system or the communication agents that are part of the system modules and/or the modular devices may send responses to the queries received from the controller 40002. For example, a communication agent that may be part of a system module or a modular device may send a response message in response to a Get or a Set message or messages similar to the Get or the Set messages received from the controller 40002. In an example, in response to a Get message or a similar message received from the controller 40002, the response message from the system module or the modular device 40012a through 40012n may include the data requested. In an example, in response to a Set message or a similar message received from a system module or a modular device 40012a through 40012n, the response message from the controller 40002 may include the newly set value as confirmation that the value has been set.

A trap or a notification message or a message similar to the trap or the notification message may be used by a system module or a modular device 40012a through 40012n to provide information about events associated with the system modules or the modular devices. For example, a trap or a notification message may be sent from a system module or a modular device 40012a through 40012n to the controller 40002 indicating a status of a communication interface (e.g., whether it available or unavailable for communication). The controller 40002 may send a receipt of the trap message back to the system module or the modular device 40012a through 40012n (e.g., to the agent on the system module or a modular device).

In an example, TELNET protocol may be used to provide a bidirectional interactive text-oriented communication facility between system modules and/or modular devices 40012a through 40012n and the controller 40002. TELNET protocol may be used to collect status information and/or send configuration data (e.g., control programs) from/to the controller 40002. TELNET may be used by one of the management applications 40014 or 40016 to establish a connection with the controller 40002 using the transmission control protocol port number 23.

In an example, SSH, a cryptographic encrypted protocol, may be used to allow remote login and to collect status information and/or send configuration data about system modules and/or modular devices 40012a through 40012n from/to the controller 40002. SSH may be used by one of the management applications 40014 or 40016 to establish an encrypted connection with the controller 40002 using the transmission control protocol port number 22.

In an example, NETCONF may be used to perform management functions by invoking remote procedure calls using, for example, <rpc>, <rpc-reply>, or <edit-config> operations. The <rpc> and <rpc-reply> procedure calls or similar procedure calls may be used for exchanging information from a system module and/or a modular device associated with a surgical system. The NETCONF <edit-config> operation or a similar operation may be used for configuring the system modules and/or the modular devices associated with the surgical system.

The controller 40002 may configure the system modules and/or modular device 40012a through 40012n to establish a data plane 40010. The data plane 40010 (e.g., also referred to as a user plane or a forwarding plane) may enable a communication data path between a plurality of system modules and/or modular device 40012a through 40012n. The data plane 40010 may be utilized by the system modules and/or the modular device 40012a through 40012n for communicating data flows of data between the system modules and/or modular devices associated with a surgical system. The data flows may be established using one or more dedicated communication interfaces between the system modules and/or the modular devices associated with one or more surgical hubs of a surgical system. In an example, the data flows may be established over one or more local area networks (LANs) and one or more wide area networks (WANs), such as the Internet.

In an example, the data plane 40010 may provide support for establishing a first and a second independent, disjointed, concurrent, and redundant communication path for data flow between the system modules and/or modular devices 40012b and 40012n. As illustrated in FIG. 1C, redundant communication paths may be established between system modules/modular devices 40012b and 40012n. The redundant communication paths may carry same/redundant data flows between the system modules and/or modular devices. In an example, when or if some of the data packets are dropped on one of the redundant communication paths due to problems with one of the communication interfaces on the system modules/modular devices 40012b and 40012n, the system modules and/or the modular devices may continue to send/receive at least one copy of the dropped data packets over the second communication path.

Figure 2:
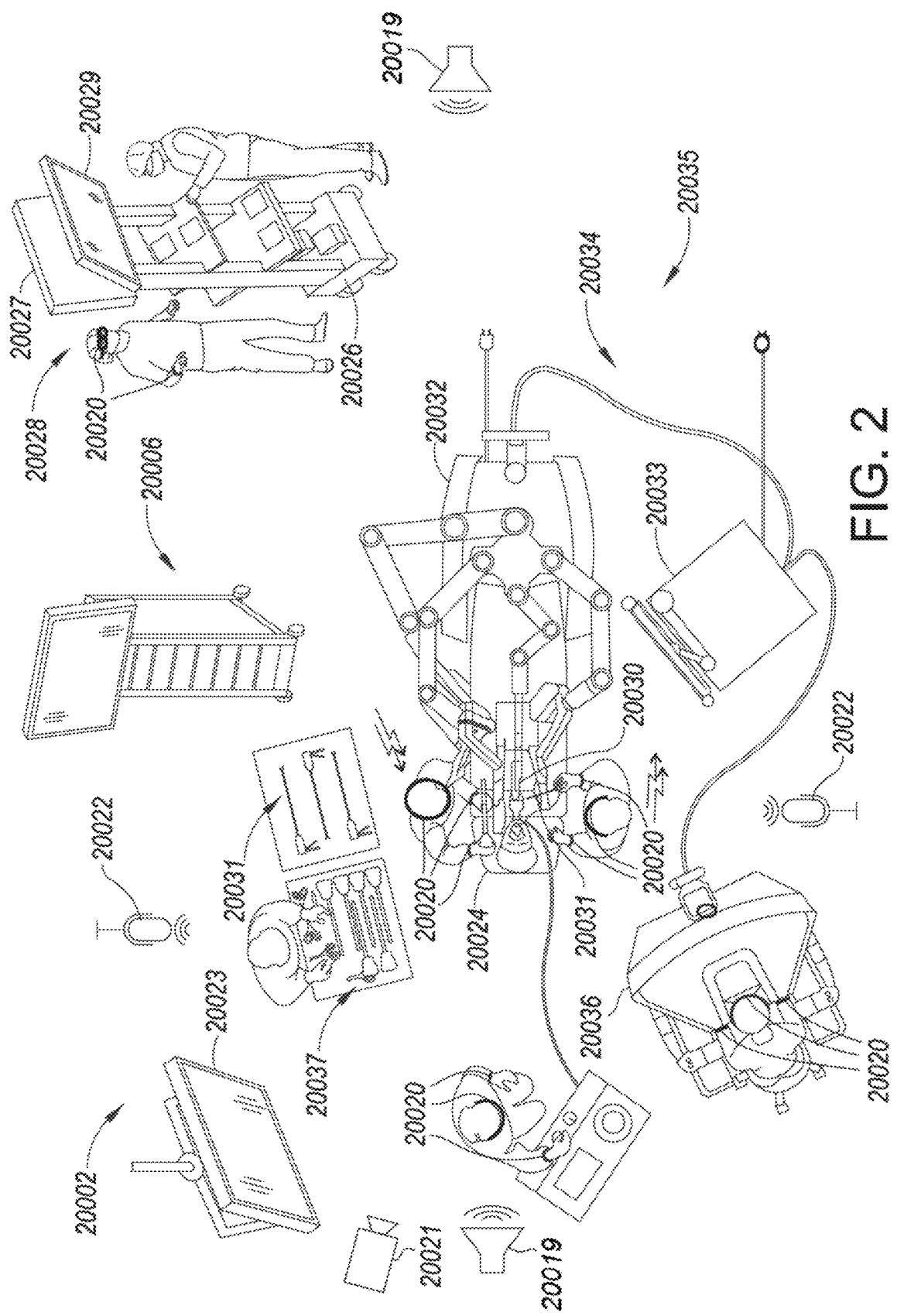
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1A. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 2002.3. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1A may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 21006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
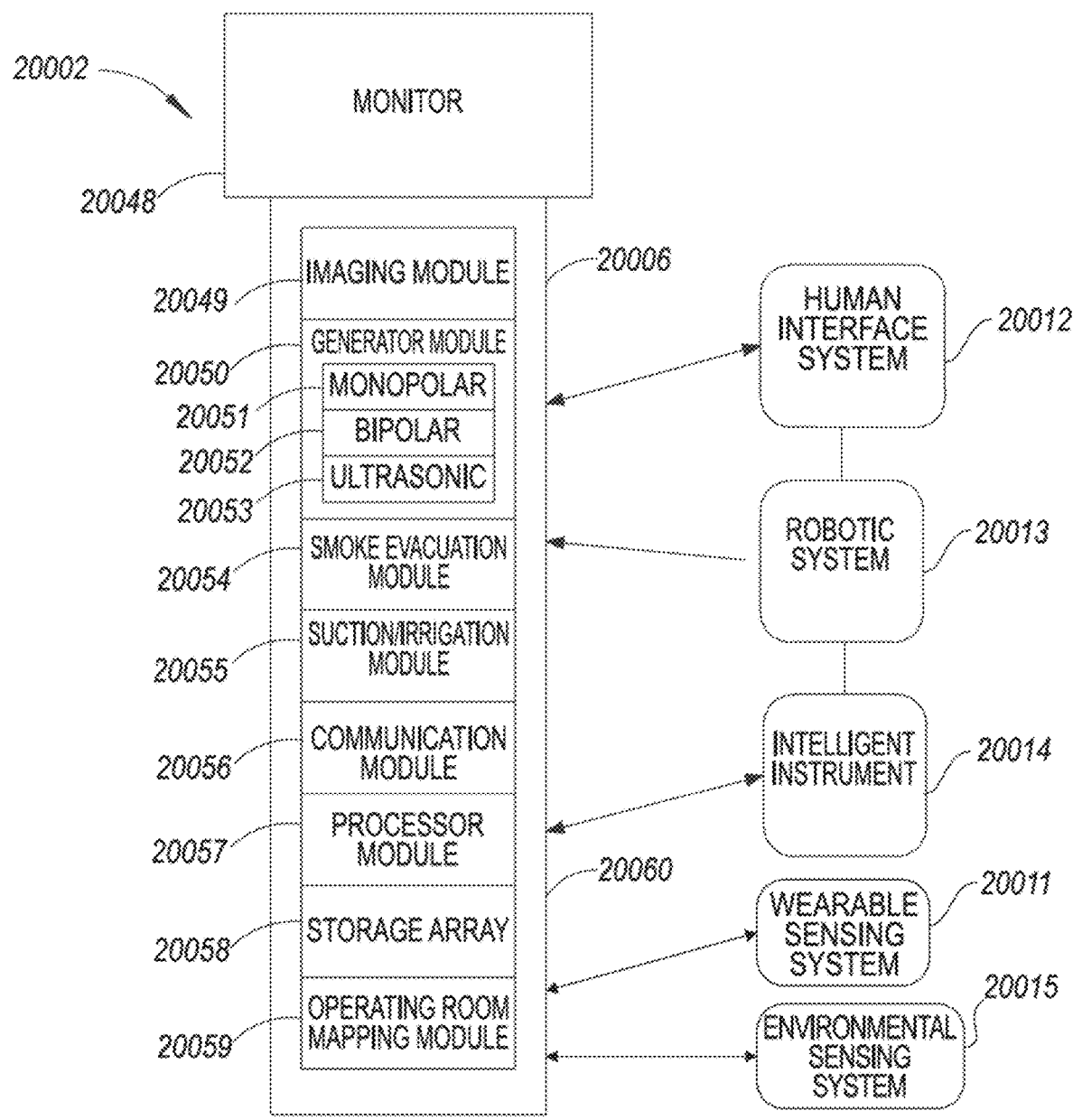
FIG. 3 illustrates an example surgical hub paired with various systems.

FIG. 3 shows an example surgical system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20000. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20006 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
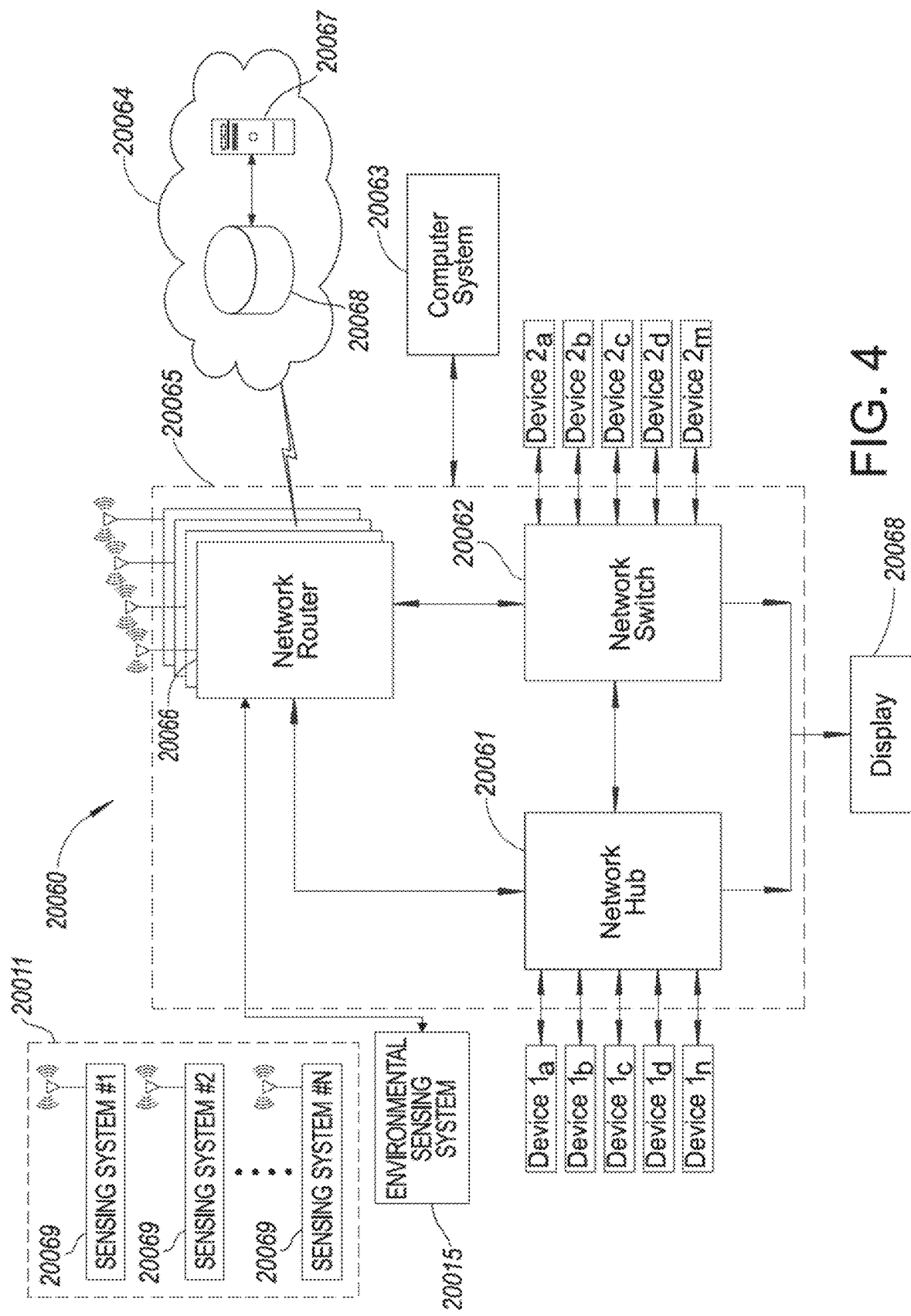
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellar-isWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20009 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OST) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 2066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any (other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
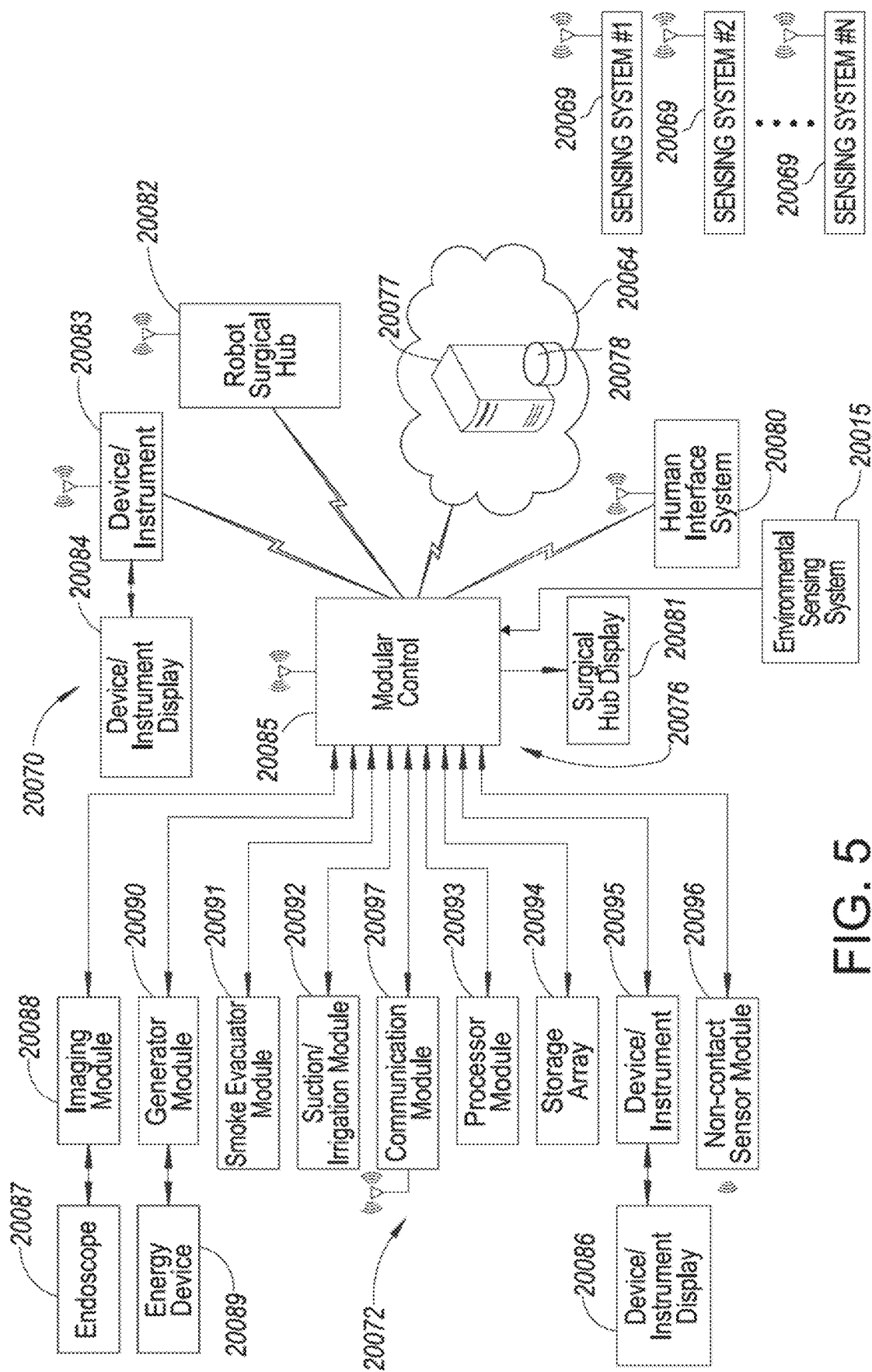
FIG. 5 illustrates an example computer-implemented interactive surgical system that may be part of a surgical system.

FIG. 5 illustrates a computer-implemented interactive surgical system 20070 that may be a part of the Surgical system 20002. The computer-implemented interactive surgical system 20070 is similar in many respects to the HCP sensing system 20002. For example, the computer-implemented interactive surgical system 20070 may include one or more surgical sub-systems 20072, which are similar in many respects to the Surgical systems 20002. Each sub-surgical system 20072 may include at least one surgical hub 20076 in communication with a cloud computing system 20064 that may include a remote server 20077 and a remote storage 20078. In one aspect, the computer-implemented interactive surgical system 20070 may include a modular control 20085 connected to multiple operating theater devices such as sensing systems 20001, intelligent surgical instruments, robots, and other computerized devices located in the operating theater.

As illustrated in the example of FIG. 5, the modular control 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The non-contact sensor module 20096 may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The modular control 20085 may also be in communication with one or more sensing systems 20069 and an environmental sensing system 20015. The sensing systems 20069 may be connected to the modular control 20085 either directly via a router or via the communication module 20097. The operating theater devices may be coupled to cloud computing resources and data storage via the modular control 20085. A robot surgical hub 20082 also may be connected to the modular control 20085 and to the cloud computing resources. The devices/instruments 20095 or 20084, human interface system 20080, among others, may be coupled to the modular control 20085 via wired or wireless communication standards or protocols, as described herein. The human interface system 20080 may include a display sub-system and a notification sub-system. The modular control 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control 20085 in conjunction with images and overlaid images.

Figure 6:
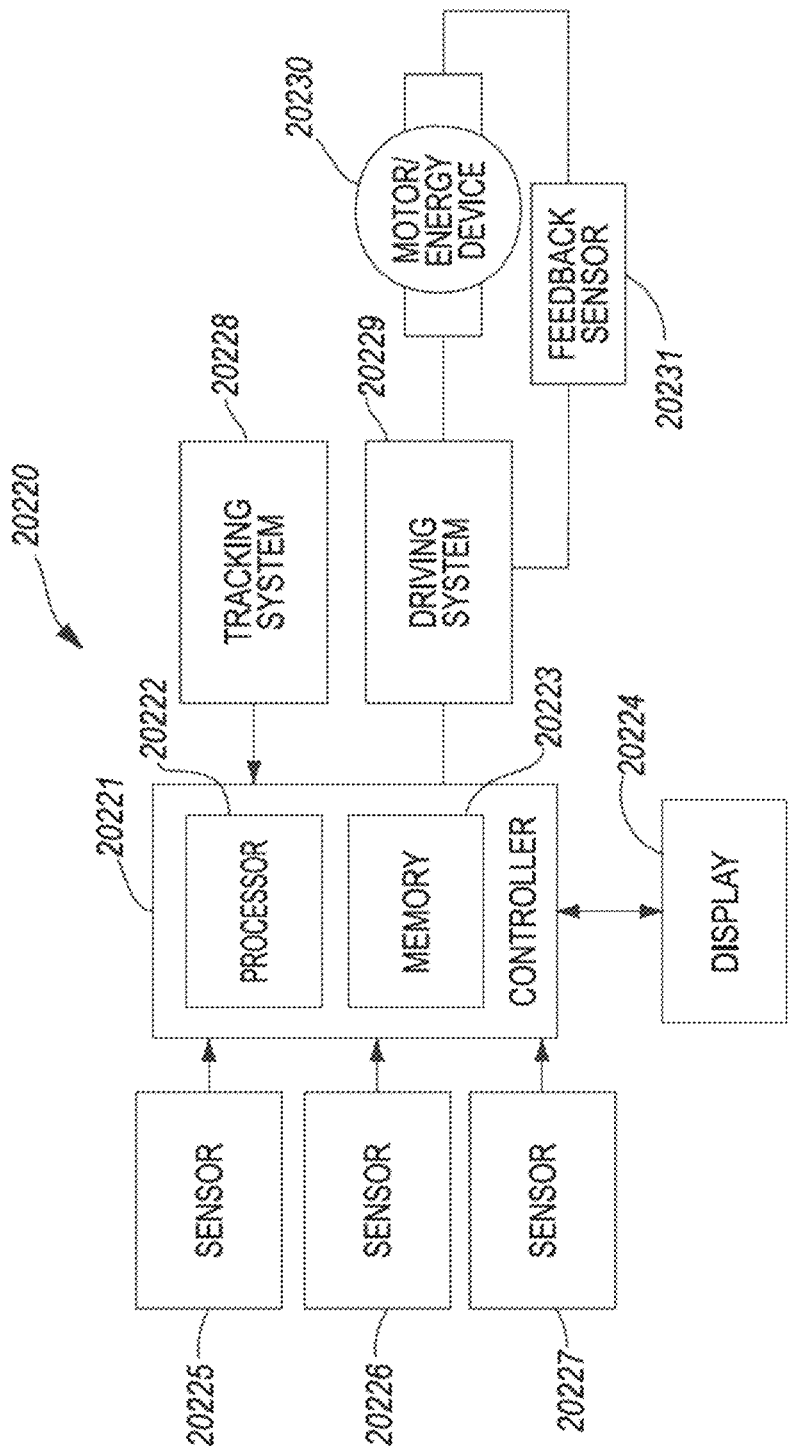
FIG. 6 illustrates a logic diagram of a control system of a surgical instrument.

FIG. 6 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPMI. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+ d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 201225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 21226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5.

Figure 7:
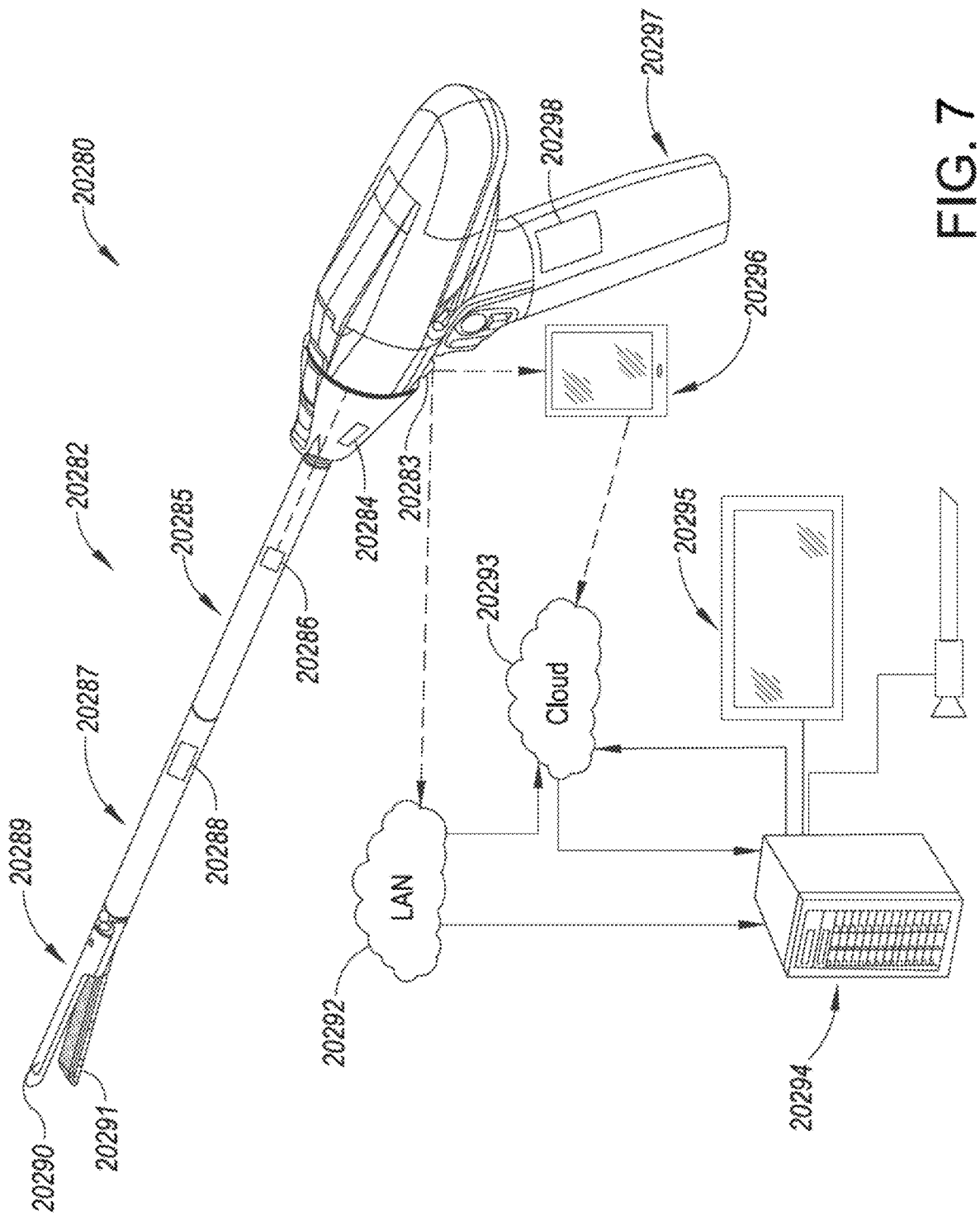
FIG. 7 shows an example surgical system that includes a handle having a controller and a motor, an adapter releasably coupled to the handle, and a loading unit releasably coupled to the adapter.

FIG. 7 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 21285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second law 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 8:
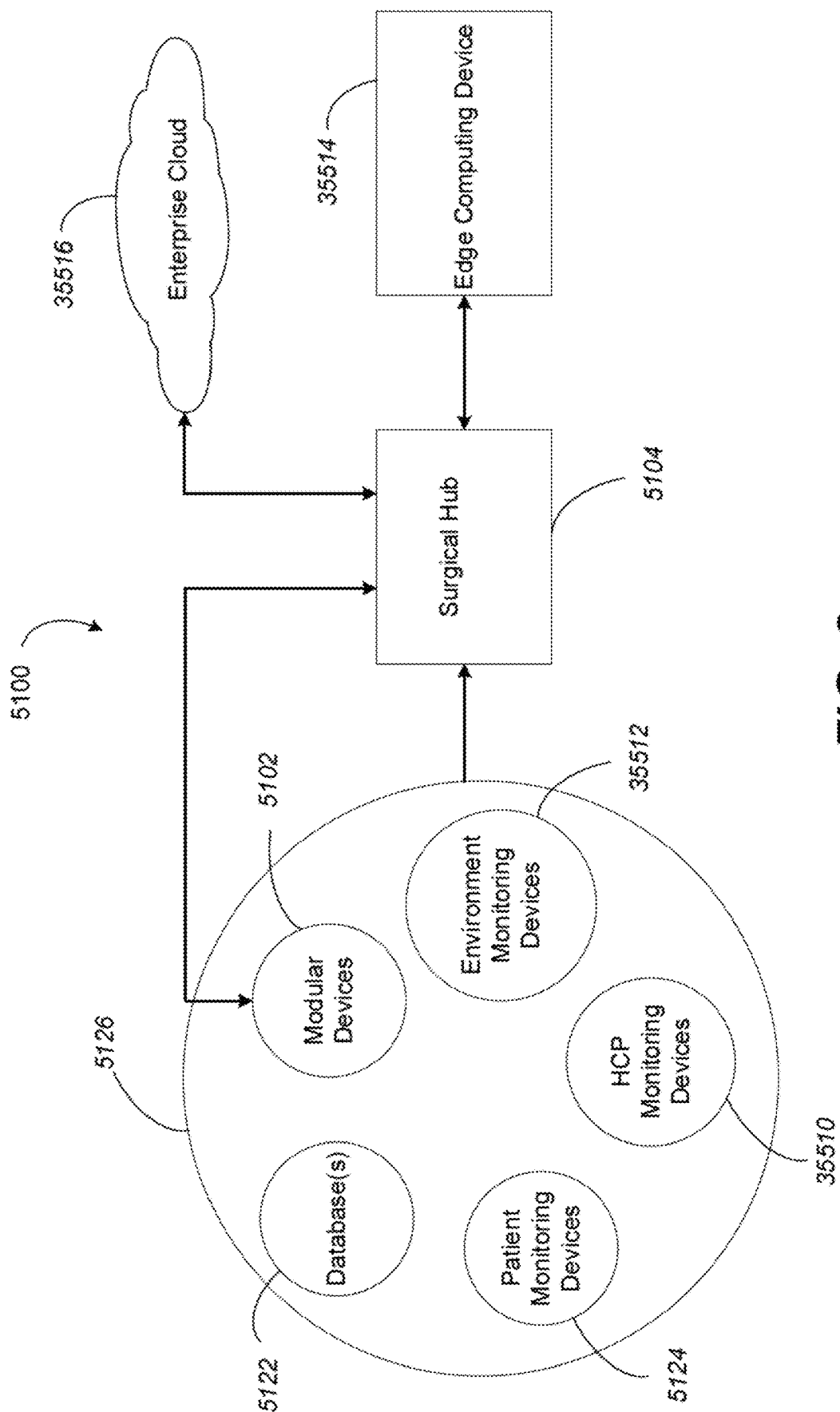
FIG. 8 shows an example situationally aware surgical system.

FIG. 8 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be con figured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub

5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

A computing system may use redundant communication pathways for communicating surgical imaging feed(s). For example, surgical video feed(s) may be sent via multiple video stream pathways to improve resilience of the feed.

Figure 9A:
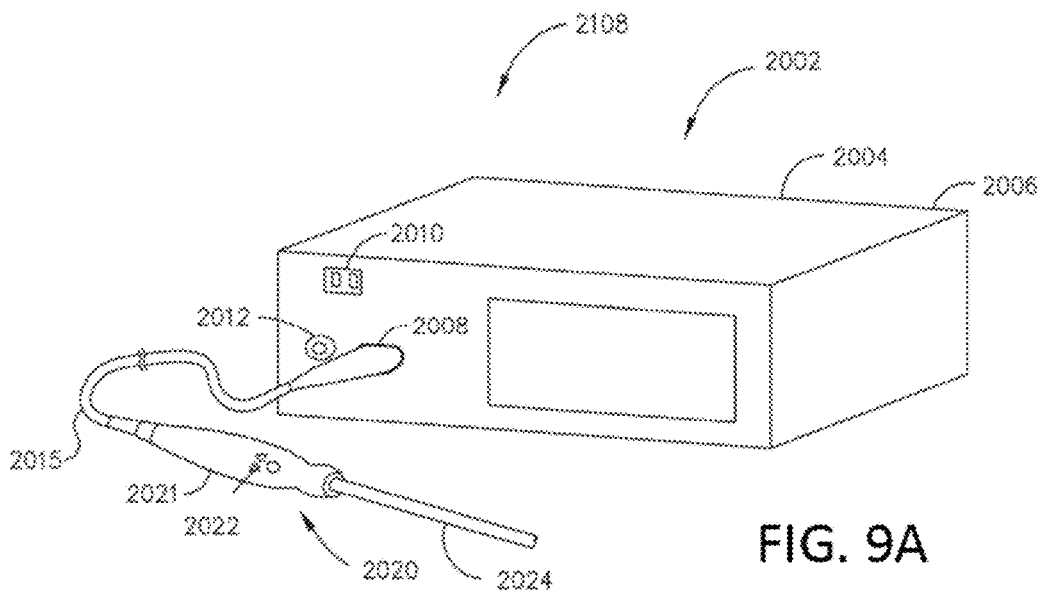
FIGS. 9A-9C show an example visualization system.
Figure 9B:
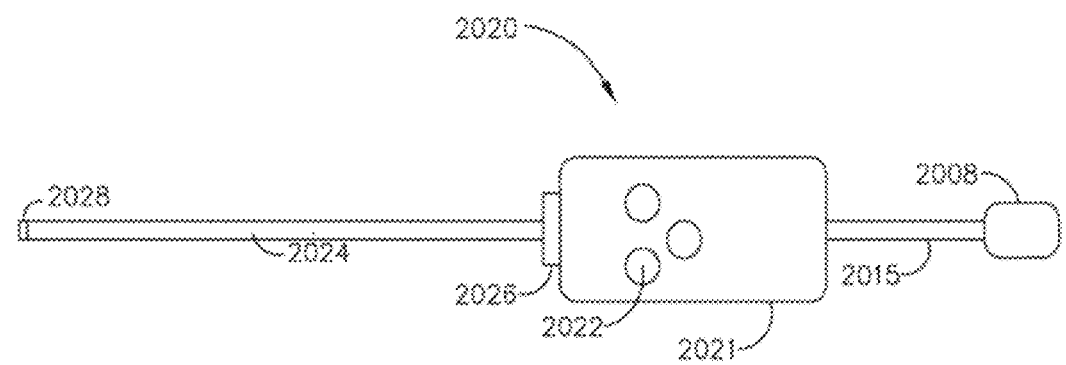
Figure 9C:
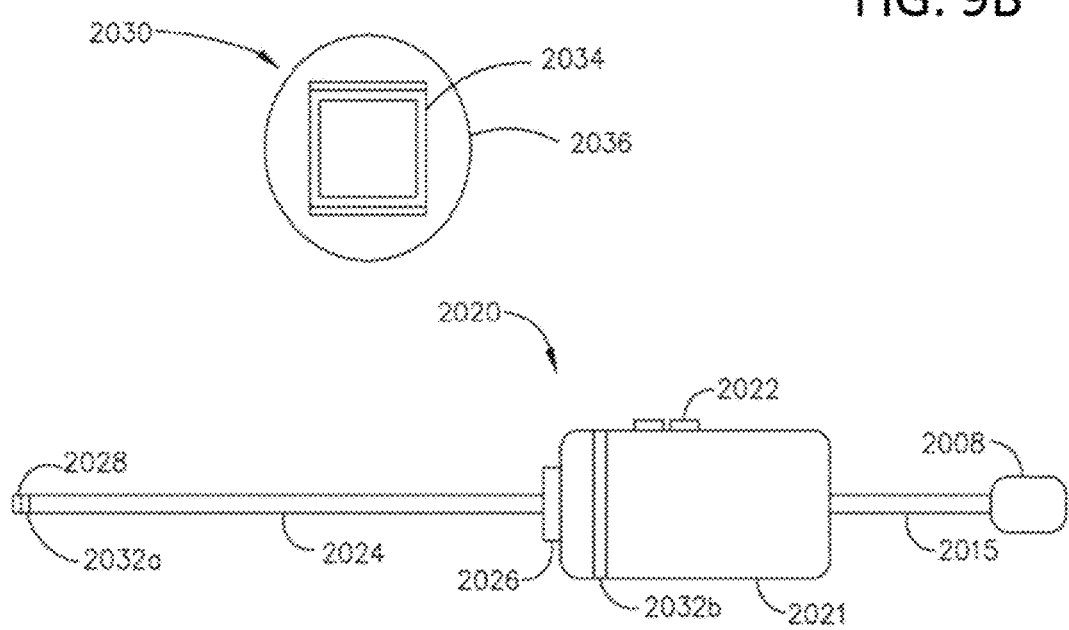

FIGS. 9A-9C show an example visualization system 2108 that may be incorporated into a surgical system. The visualization system 2108 may include an imaging control unit 2002 and a hand unit 2020. The imaging control unit 2002 may include one or more illumination sources, a power supply for the one or more illumination sources, one or more types of data communication interfaces (including USB, Ethernet, or wireless interfaces 2004), and one or more video outputs 2006. The imaging control unit 2002 may further include an interface, such as a USB interface 2010, configured to transmit integrated video and image capture data to a USB enabled device. The imaging control unit 2002 may also include one or more computational components including, without limitation, a processor unit, a transitory memory unit, a non-transitory memory unit, an image processing unit, a bus structure to form data links among the computational components, and any interface (e.g. input and/or output) devices necessary to receive information from and transmit information to components not included in the imaging control unit. The non-transitory memory may further contain instructions that when executed by the processor unit, may perform any number of manipulations of data that may be received from the hand unit 2020 and/or computational devices not included in the imaging control unit.

The illumination sources may include a white light source 2012 and one or more laser light sources. The imaging control unit 2002 may include one or more optical and/or electrical interfaces for optical and/or electrical communication with the hand unit 2020. The one or more laser light sources may include, as non-limiting examples, any one or more of a red laser light source, a green laser light source, a blue laser light source, an infrared laser light source, and an ultraviolet laser light source. In some non-limiting examples, the red laser light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some non-limiting examples, the green laser light source may source illumination having a peak wavelength that may range between 520 nm and 532 nm, inclusive. Non-limiting examples of a green laser peak wavelength may include about 520 nm, about 522 nm, about 524 nm, about 526 nm, about 528 nm, about 530 nm, about 532 nm, or any value or range of values therebetween. In some non-limiting examples, the blue laser light source may source illumination having a peak wavelength that may range between 405 nm and 445 nm, inclusive. Non-limiting examples of a blue laser peak wavelength may include about 405 nm, about 410 nm, about 415 nm, about 420 nm, about 425 nm, about 430 nm, about 435 nm, about 440 nm, about 445 nm, or any value or range of values therebetween. In some non-limiting examples, the infrared laser light source may source illumination having a peak wavelength that may range between 750 nm and 3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. In some non-limiting examples, the ultraviolet laser light source may source illumination having a peak wavelength that may range between 200 nm and 360 nm, inclusive. Non-limiting examples of an ultraviolet laser peak wavelength may include about 200 nm, about 220 nm, about 240 nm, about 260 nm, about 280 nm, about 300 nm, about 320 nm, about 340 nm, about 360 nm, or any value or range of values therebetween.

The hand unit 2020 may include a body 2021, a camera scope cable 2015 attached to the body 2021, and an elongated camera probe 2024. The body 2021 of the hand unit 2020 may include hand unit control buttons 2022 or other controls to permit a health professional using the hand unit 2020 to control the operations of the hand unit 2020 or other components of the imaging control unit 2002, including, for example, the light sources. The camera scope cable 2015 may include one or more electrical conductors and one or more optical fibers. The camera scope cable 2015 may terminate with a camera head connector 2008 at a proximal end in which the camera head connector 2008 is configured to mate with the one or more optical and/or electrical interfaces of the imaging control unit 2002. The electrical conductors may supply power to the hand unit 2020, including the body 2021 and the elongated camera probe 2024, and/or to any electrical components internal to the hand unit 2020 including the body 2021 and/or elongated camera probe 2024. The electrical conductors may also serve to provide bi-directional data communication between any one or more components the hand unit 2020 and the imaging control unit 2002. The one or more optical fibers may conduct illumination from the one or more illumination sources in the imaging control unit 2002 through the hand unit body 2021 and to a distal end of the elongated camera probe 2024. In some non-limiting aspects, the one or more optical fibers may also conduct light reflected or refracted from the surgical site to one or more optical sensors disposed in the elongated camera probe 2024, the hand unit body 2021, and/or the imaging control unit 2002.

FIG. 9B (a top plan view) depicts in more detail some aspects of a hand unit 2020 of the visualization system 2108. The hand unit body 2021 may be constructed of a plastic material. The hand unit control buttons 2022 or other controls may have a rubber overmolding to protect the controls while permitting them to be manipulated by the surgeon. The camera scope cable 2015 may have optical fibers integrated with electrical conductors, and the camera scope cable 2015 may have a protective and flexible overcoating such as PVC. In some non-limiting examples, the camera scope cable 2015 may be about 10 ft. long to permit ease of use during a surgical procedure. The length of the camera scope cable 2015 may range from about 5 ft. to about 15 ft. Non-limiting examples of a length of the camera scope cable 2015 may be about 5 ft., about 6 ft., about 7 ft., about 8 ft., about 9 ft., about 10 ft., about 11 ft., about 12 ft., about 13 ft., about 14 ft., about 15 ft., or any length or range of lengths therebetween. The elongated camera probe 2024 may be fabricated from a rigid material such as stainless steel. The elongated camera probe 2024 may be joined with the hand unit body 2021 via a rotatable collar 2026. The rotatable collar 2026 may permit the elongated camera probe 2024 to be rotated with respect to the hand unit body 2021. The elongated camera probe 2024 may terminate at a distal end with a plastic window 2028 sealed with epoxy.

The side plan view of the hand unit, depicted in FIG. 9C illustrates that a light or image sensor 2030 may be disposed at a distal end 2032a of the elongated camera probe or within the hand unit body 2032b. The light or image sensor 2030 may be dispose with additional optical elements in the imaging control unit 2002. FIG. 9C depicts an example of a light sensor 2030 comprising a CMOS image sensor 2034 disposed within a mount 2036 having a radius of about 4 mm. Although the CMOS image sensor in FIG. 9C is depicted to be disposed within a mount 2036 having a radius of about 4 mm, it may be recognized that such a sensor and mount combination may be of any useful size to be disposed within the elongated camera probe 2024, the hand unit body 2021, or in the image control unit 2002. Some non-limiting examples of such alternative mounts may include a 5.5 mm mount 2136, a 4 mm mount 2136, a 2.7 mm mount 2136, and a 2 mm mount 2136. It may be recognized that the image sensor may also comprise a CCD image sensor. The CMOS or CCD sensor may comprise an array of individual light sensing elements (pixels).

During a surgical procedure, a surgeon may be required to manipulate tissues to affect a desired medical outcome. The actions of the surgeon are limited by what is visually observable in the surgical site. Thus, the surgeon may not be aware, for example, of the disposition of vascular structures that underlie the tissues being manipulated during the procedure.

Since the surgeon is unable to visualize the vasculature beneath a surgical site, the surgeon may accidentally sever one or more critical blood vessels during the procedure.

Therefore, it is desirable to have a surgical visualization system that can acquire imaging data of the surgical site for presentation to a surgeon in which the presentation can include information related to the presence of vascular structures located beneath the surface of a surgical site.

Some aspects of the present disclosure further provide for a control circuit configured to control the illumination of a surgical site using one or more illumination sources such as laser light sources and to receive imaging data from one or more image sensors. In some aspects, the present disclosure provides for a non-transitory computer readable medium storing computer readable instructions that, when executed, cause a device to detect a blood vessel in a tissue and determine its depth below the surface of the tissue.

In some aspects, a surgical image acquisition system may include a plurality of illumination sources wherein each illumination source is configured to emit light having a specified central wavelength, a light sensor configured to receive a portion of the light reflected from a tissue sample when illuminated by the one or more of the plurality of illumination sources, and a computing system. The computing system may be configured to: receive data from the light sensor when the tissue sample is illuminated by each of the plurality of illumination sources; determine a depth location of a structure within the tissue sample based on the data received by the light sensor when the tissue sample is illuminated by each of the plurality of illumination sources, and calculate visualization data regarding the structure and the depth location of the structure. In some aspects, the visualization data may have a data format that may be used by a display system, and the structure may comprise one or more vascular tissues.

In an aspect, a surgical image acquisition system may include an independent color cascade of illumination sources comprising visible light and light outside of the visible range to image one or more tissues within a surgical site at different times and at different depths. The surgical image acquisition system may further detect or calculate characteristics of the light reflected and/or refracted from the surgical site. The characteristics of the light may be used to provide a composite image of the tissue within the surgical site as well as provide an analysis of underlying tissue not directly visible at the surface of the surgical site. The surgical image acquisition system may determine tissue depth location without the need for separate measurement devices.

In an aspect, the characteristic of the light reflected and/or refracted from the surgical site may be an amount of absorbance of light at one or more wavelengths. Various chemical components of individual tissues may result in specific patterns of light absorption that are wavelength dependent.

In one aspect, the illumination sources may comprise a red laser source and a near infrared laser source, wherein the one or more tissues to be imaged may include vascular tissue such as veins or arteries. In some aspects, red laser sources (in the visible range) may be used to image some aspects of underlying vascular tissue based on spectroscopy in the visible red range. In some non-limiting examples, a red laser light source may source illumination having a peak wavelength that may range between 635 nm and 660 nm, inclusive. Non-limiting examples of a red laser peak wavelength may include about 635 nm, about (40 nm, about 645 nm, about 650 nm, about 655 nm, about 660) nm, or any value or range of values therebetween. In some other aspects, near infrared laser sources may be used to image underlying vascular tissue based on near infrared spectroscopy. In some non-limiting examples, a near infrared laser source may emit illumination have a wavelength that may range between 750-3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. It may be recognized that underlying vascular tissue may be probed using a combination of red and infrared spectroscopy. In some examples, vascular tissue may be probed using a red laser source having a peak wavelength at about 660 nm and a near IR laser source having a peak wavelength at about 750 nm or at about 850 nm.

Near infrared spectroscopy (NIRS) is a non-invasive technique that allows determination of tissue oxygenation based on spectro-photometric quantitation of oxy- and deoxyhemoglobin within a tissue. In some aspects, NIRS can be used to image vascular tissue directly based on the difference in illumination absorbance between the vascular tissue and non-vascular tissue. Alternatively, vascular tissue can be indirectly visualized based on a difference of illumination absorbance of blood flow in the tissue before and after the application of physiological interventions, such as arterial and venous occlusions methods.

Instrumentation for near-IR (NIR) spectroscopy may be similar to instruments for the UV-visible and mid-IR ranges. Such spectroscopic instruments may include an illumination source, a detector, and a dispersive element to select a specific near-IR wavelength for illuminating the tissue sample. In some aspects, the source may comprise an incandescent light source or a quartz halogen light source. In some aspects, the detector may comprise semiconductor (for example, an InGaAs) photodiode or photo array. In some aspects, the dispersive element may comprise a prism or, more commonly, a diffraction grating. Fourier transform NIR instruments using an interferometer are also common, especially for wavelengths greater than about 1000 nm. Depending on the sample, the spectrum can be measured in either reflection or transmission mode.

Figure 10:
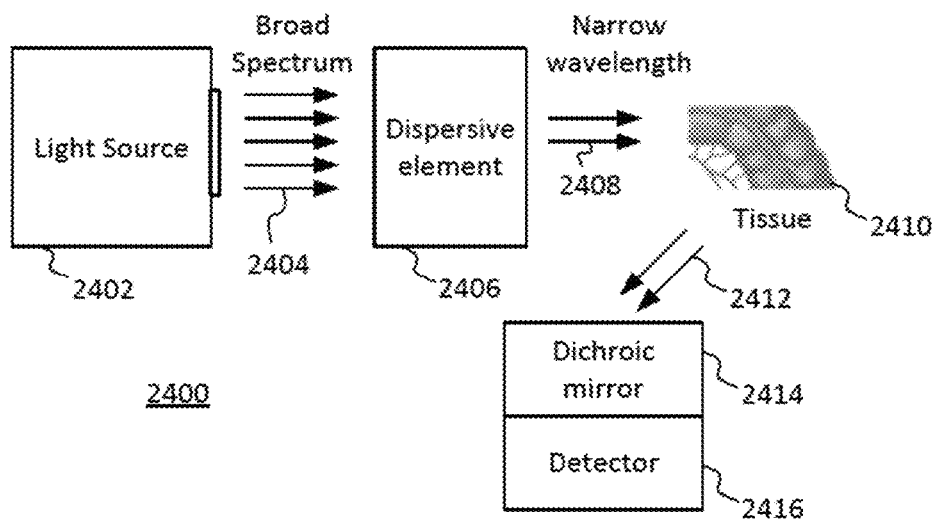
FIG. 10 illustrates example instrumentation for near infrared spectroscopy (NIRS) spectroscopy.

FIG. 10 depicts schematically one example of instrumentation 2400 similar to instruments for the UV-visible and mid-IR ranges for NIR spectroscopy. A light source 2402 may emit a broad spectral range of illumination 2404 that may impinge upon a dispersive element 2406 (such as a prism or a diffraction grating). The dispersive element 2406 may operate to select a narrow wavelength portion 2408 of the light emitted by the broad spectrum light source 2402, and the selected portion 2408 of the light may illuminate the tissue 2410. The light reflected from the tissue 2412 may be directed to a detector 2416 (for example, by means of a dichroic mirror 2414) and the intensity of the reflected light 2412 may be recorded. The wavelength of the light illuminating the tissue 2410 may be selected by the dispersive element 2406. In some aspects, the tissue 2410 may be illuminated only by a single narrow wavelength portion 2408 selected by the dispersive element 2406 form the light source 2402. In other aspects, the tissue 2410 may be scanned with a variety of narrow wavelength portions 2408 selected by the dispersive element 2406. In this manner, a spectroscopic analysis of the tissue 2410 may be obtained over a range of NIR wavelengths.

Figure 11:
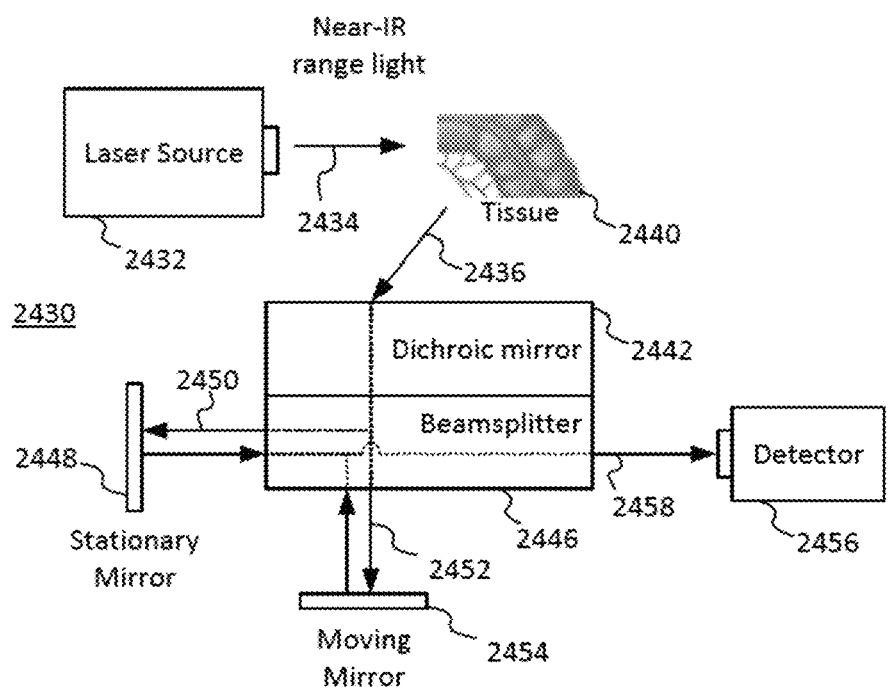
FIG. 11 illustrates example instrumentation for determining NIRS based on Fourier transform infrared imaging.

FIG. 11 depicts schematically one example of instrumentation 2430 for determining NIRS based on Fourier transform infrared imaging. In FIG. 11, a laser source emitting 2432 light in the near IR range 2434 illuminates a tissue sample 2440. The light reflected 2436 by the tissue 2440 is reflected by a mirror, such as a dichroic mirror 2444, to a beam splitter 2446. The beam splitter 2446 directs one portion of the light 2448 reflected by the tissue 2440 to a stationary mirror 2450 and one portion of the light 2452 reflected 2436 by the tissue 2440 a moving mirror 2454. The moving mirror 2454 may oscillate in position based on an affixed piezoelectric transducer activated by a sinusoidal voltage having a voltage frequency. The position of the moving mirror 2454 in space corresponds to the frequency of the sinusoidal activation voltage of the piezoelectric transducer. The light reflected from the moving mirror and the stationary mirror may be recombined 2458 at the beam splitter 2446 and directed to a detector 2456. Computational components may receive the signal output of the detector 2456 and perform a Fourier transform (in time) of the received signal. Because the wavelength of the light received from the moving mirror 2454 varies in time with respect to the wavelength of the light received from the stationary mirror 2450, the time-based Fourier transform of the recombined light corresponds to a wavelength-based Fourier transform of the recombined light 2458. In this manner, a wavelength-based spectrum of the light reflected from the tissue 2440 may be determined and spectral characteristics of the light reflected 2436 from the tissue 2440 may be obtained. Changes in the absorbance of the illumination in spectral components from the light reflected from the tissue 2440 may thus indicate the presence or absence of tissue having specific light absorbing properties (such as hemoglobin).

An alternative to near infrared light to determine hemoglobin oxygenation would be the use of monochromatic red light to determine the red light absorbance characteristics of hemoglobin. The absorbance characteristics of red light having a central wavelength of about 660 nm by the hemoglobin may indicate if the hemoglobin is oxygenated (arterial blood) or deoxygenated (venous blood).

In some alternative surgical procedures, contrasting agents can be used to improve the data that is collected on oxygenation and tissue oxygen consumption. In one non-limiting example, NIRS techniques may be used in conjunction with a bolus injection of a near-IR contrast agent such as indocyanine green (ICG) which has a peak absorbance at about 800 nm. ICG has been used in some medical procedures to measure cerebral blood flow.

In one aspect, the characteristic of the light reflected and/or refracted from the surgical site may be a Doppler shift of the light wavelength from its illumination source.

Laser Doppler flowmetry may be used to visualize and characterized a flow of particles moving relative to an effectively stationary background. Thus, laser light scattered by moving particles, such as blood cells, may have a different wavelength than that of the original illuminating laser source. In contrast, laser light scattered by the effectively stationary background (for example, the vascular tissue) may have the same wavelength of that of the original illuminating laser source. The change in wavelength of the scattered light from the blood cells may reflect both the direction of the flow of the blood cells relative to the laser source as well as the blood cell velocity.

Figure 12:
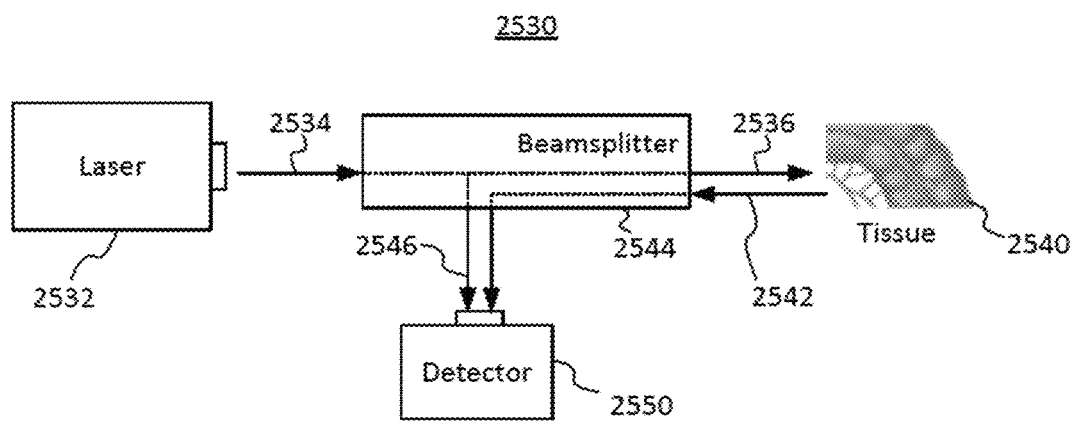
FIG. 12 illustrates example instrumentation that may be used to detect a Doppler shift in laser light scattered from portions of a tissue.

FIG. 12 depicts an aspect of instrumentation 2530 that may be used to detect a Doppler shift in laser light scattered from portions of a tissue 2540. Light 2534 originating from a laser 2532 may pass through a beam splitter 2544. Some portion of the laser light 2536 may be transmitted by the beam splitter 2544 and may illuminate tissue 2540. Another portion of the laser light may be reflected 2546 by the beam splitter 2544 to impinge on a detector 2550. The light back-scattered 2542 by the tissue 2540 may be directed by the beam splitter 2544 and also impinge on the detector 2550. The combination of the light 2534 originating from the laser 2532 with the light back-scattered 2542 by the tissue 2540 may result in an interference pattern detected by the detector 2550. The interference pattern received by the detector 2550 may include interference fringes resulting from the combination of the light 2534 originating from the laser 2532 and the Doppler shifted (and thus wavelength shifted) light back-scattered 2452 from the tissue 2540.

It may be recognized that back-scattered light 2542 from the tissue 2540 may also include back scattered light from boundary layers within the tissue 2540 and/or wavelength-specific light absorption by material within the tissue 254). As a result, the interference pattern observed at the detector 2550 may incorporate interference fringe features from these additional optical effects and may therefore confound the calculation of the Doppler shift unless properly analyzed.

Figure 13:
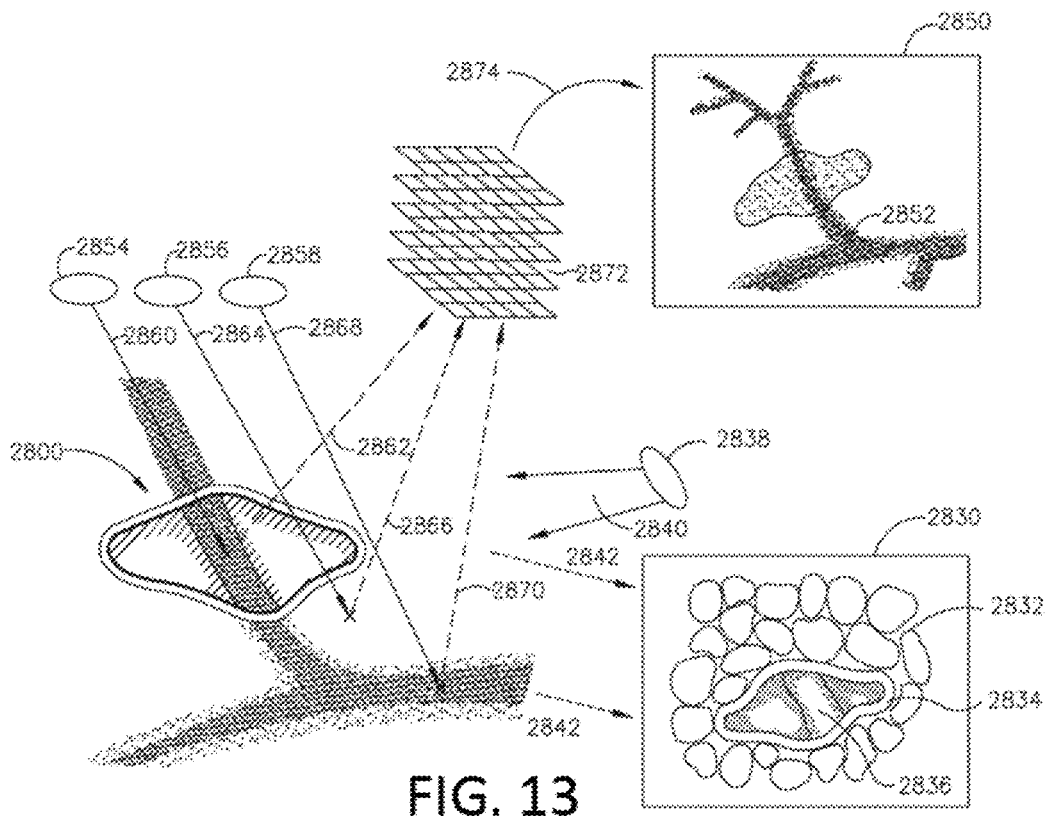
FIG. 13 illustrates an example composite image comprising a sur face image and an image of a subsurface blood vessel.

FIG. 13 depicts an aspect of a composite visual display 2800 that may be presented a surgeon during a surgical procedure. The composite visual display 2800 may be constructed by overlaying a white light image 2830 of the surgical site with a Doppler analysis image 2850.

The white light image 2830 may portray the surgical site 2832, one or more surgical incisions 2834, and the tissue 2836 readily visible within the surgical incision 2834. The white light image 2830 may be generated by illuminating 2840 the surgical site 2832 with a white light source 2838 and receiving the reflected white light 2842 by an optical detector. Although a white light source 2838 may be used to illuminate the surface of the surgical site, in one aspect, the surface of the surgical site may be visualized using appropriate combinations of red 2854, green 2856, and blue 2858 laser light.

The Doppler analysis image 2850 may include blood vessel depth information along with blood flow information 2852 (from speckle analysis). Blood vessel depth and blood flow velocity may be obtained by illuminating the surgical site with laser light of multiple wavelengths, and determining the blood vessel depth and blood flow based on the known penetration depth of the light of a particular wavelength. In general, the surgical site 2832 may be illuminated by light emitted by one or more lasers such as a red leaser 2854, a green laser 2856, and a blue laser 2858. A CMOS detector 2872 may receive the light reflected back (2862, 2866, 2870) from the surgical site 2832 and its surrounding tissue. The Doppler analysis image 2850 may be constructed 2874 based on an analysis of the multiple pixel data from the CMOS detector 2872.

For example, a red laser 2854 may emit red laser illumination 2860 on the surgical site 2832 and the reflected light 2862 may reveal surface or minimally subsurface structures. In one aspect, a green laser 2856 may emit green laser illumination 2864 on the surgical site 2832 and the reflected light 2866 may reveal deeper subsurface characteristics. In another aspect, a blue laser 2858 may emit blue laser illumination 2868 on the surgical site 2832 and the reflected light 2870 may reveal, for example, blood flow within deeper vascular structures. The speckle contrast analysis my present the surgeon with information regarding the amount and velocity of blood flow through the deeper vascular structures.

Although not depicted in FIG. 13 it may be understood that the imaging system may also illuminate the surgical site with light outside of the visible range. Such light may include infra-red light and ultraviolet light. In some aspects, sources of the infra-red light or ultraviolet light may include broad-band wavelength sources (such as a tungsten source, a tungsten-halogen source, or a deuterium source). In some other aspects, the sources of the infra-red or ultraviolet light may include narrow-band wavelength sources (IR diode lasers, UV gas lasers or dye lasers).

The depth of a surface feature in a piece of tissue may be determined. An image acquisition system may illuminate a tissue with a first light beam having a first central frequency and receive a first reflected light from the tissue illuminated by the first light beam. The image acquisition system may then calculate a first Doppler shift based on the first light beam and the first reflected light. The image acquisition system may then illuminate the tissue with a second light beam having a second central frequency and receive a second reflected light from the tissue illuminated by the second light beam. The image acquisition system may then calculate a second Doppler shift based on the second light beam and the second reflected light. The image acquisition system may then calculate a depth of a tissue feature based at least in part on the first central wavelength, the first Doppler shift, the second central wavelength, and the second Doppler shift. The tissue features may include the presence of moving particles, such as blood cells moving within a blood vessel, and a direction and velocity of flow of the moving particles. It may be understood that the method may be extended to include illumination of the tissue by any one or more additional light beams. Further, the system may calculate an image comprising a combination of an image of the tissue surface and an image of the structure disposed within the tissue.

Multiple visual displays may be used. For example, a 3D display may provide a composite image displaying the combined white light (or an appropriate combination of red, green, and blue laser light) and laser Doppler image. Additional displays may provide only the white light display or a displaying showing a composite white light display and an NIRS display to visualize only the blood oxygenation response of the tissue. However, the NIRS display may not be required every cycle allowing for response of tissue.

A surgical visualization system using the imaging technologies disclosed herein may benefit from ultrahigh sampling and display frequencies. Sampling rates may be associated with the capabilities of the underlying device performing the sampling. A general-purpose computing system with software may be associated with a first range of achievable sampling rates. A pure-hardware implementation (e.g., a dedicated application specific integrated circuit, ASIC) may be associated with a second range of achievable sampling rates. The second range, associated with the pure-hardware implementation, will generally be higher (e.g., much higher) than the first range, associated with general-purpose computing software implementation.

A surgical visualization system using the imaging technologies disclosed herein may benefit from solutions that balance the higher sampling rates, associated with hardware-based implementations, with the adaptability and/or updatability of software systems. Such a surgical visualization systems may employ a mix of hardware and software solutions. For example, a surgical visualization system may employ various hardware-implemented transforms with a software selector. A surgical visualization system may also employ a field programmable gate array (FPGA). An FPGA may include a hardware device that may include one or more logic elements. These logic elements may be configured by a bitstream to implement various functions. For example, the logic elements may be configured to perform certain individual logic functions and configured to perform them with a certain order and interconnection. Once configured, the FPGA may perform its function using the hardware logic elements without further configuration. Also once configured, the FPGA may be reconfigured with a different bitstream to implement a different function. And similarly, once reconfigured, the FPGA may perform this different function using the hardware logic elements.

Figure 14:
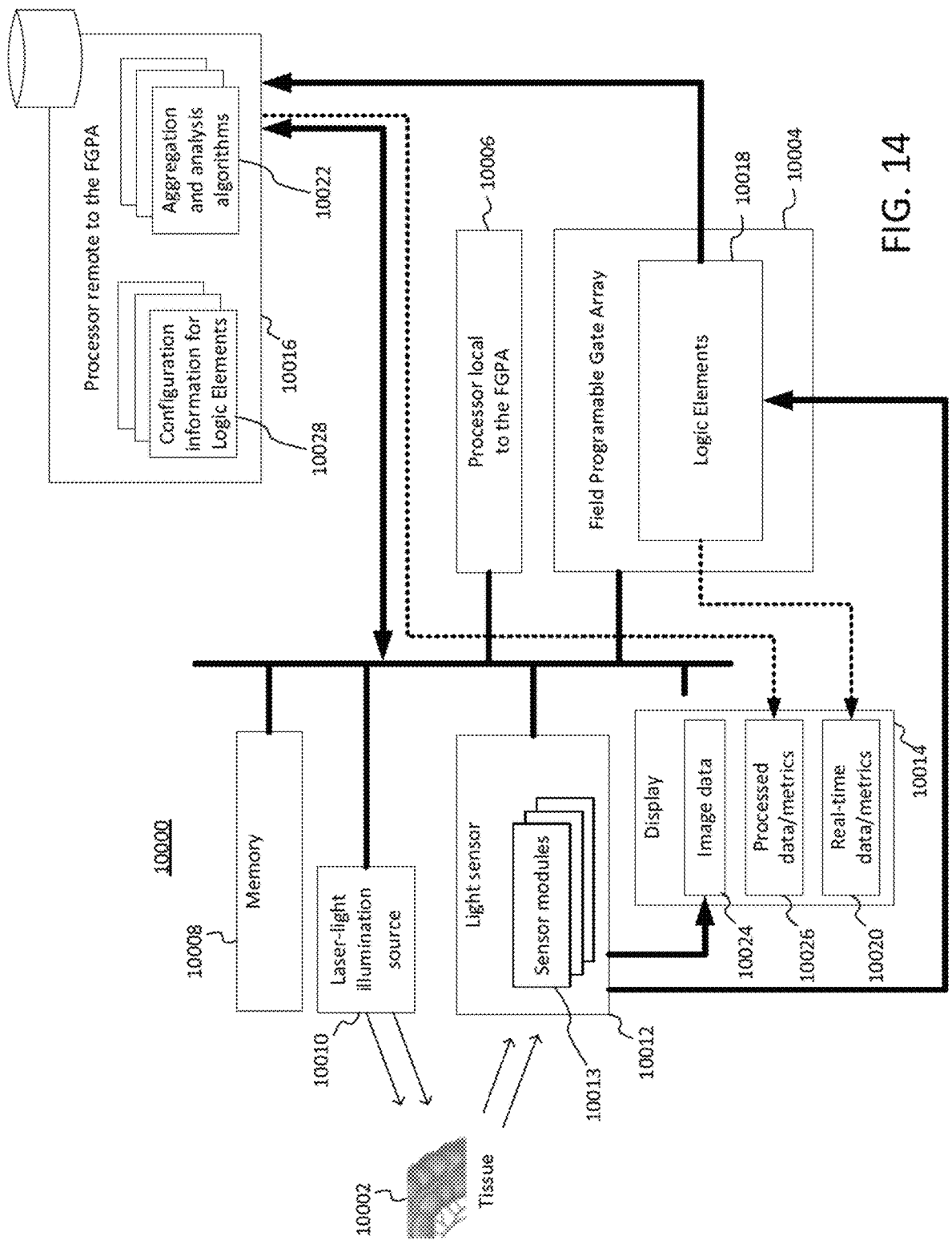
FIG. 14 illustrates an example visualization system.

FIG. 14 illustrates an example surgical visualization system 10000. The surgical visualization system 10000 may be used to analyze at least a portion of a surgical field. For example, the surgical visualization system 10000 may be used to analyze tissue 10002 within the at least a portion of the surgical field. The surgical visualization system 10000 may include an FPGA 10004, a processor (for example, a processor 10006 local to the FPGA 10004, a memory 10008, a laser-light illumination source 10010, a light sensor 10012, a display 10014, and/or a processor 10016 remote to the FGPA. The surgical visualization system 10000 may include components and functionality described in connection with FIGS. 9A-C for example.

The system 10000 may use an FPGA 10004 to convert the reflected laser light through a transform of frequency to identify a Doppler shift, for example, of the light to determine moving particles. This transformed data may be displayed (e.g., displayed in real-time). It may be displayed, for example, as a graphic and/or metric 10020, representing the number of moving particles each second. The system 10000 may include communication between the processor 10006 local to the FPGA 10004 and the processor 10016 remote to the FGPA. For example, the processor 10016 remote to the FGPA 10004 may aggregate data (e.g., multiple seconds of data). And the system may be able to display that aggregation of data. For example, it may be displayed as a graphic and/or metric 10026 representing a moving trend. This graphic and/or metric 10026 may be superimposed on the real-time data. Such trend information may be used to identify occlusions, instrument vascular sealing/clamping efficiency, vascular tree overviews, even oscillating magnitudes of motion over time. The FPGA 10004 may be configured to be on-the-fly updateable, for example, updateable with different (e.g., more sophisticated) transformations. These updates may come from local or remote communication servers. These updates may, for example, change the transform's analysis from refractivity (e.g., analysis of cellular irregularities), to blood flow, to multiple simultaneous depth analysis, and the like.

The FPGA updates may include transforms that implement a variety of imaging options for the user. These imaging options may include standard combined visual light, tissue refractivity, doppler shift, motion artifact correction, improved dynamic range, improved local clarity, super resolution, NIR florescence, multi-spectral imaging, confocal laser endomicroscopy, optical coherence tomography, raman spectroscopy, photoacoustic imaging, or any combination. The imaging options may include any of the options presented in any of the following: U.S. patent application Ser. No. 15/940,742, entitled "DUAL CMOS ARRAY IMAGING," filed Mar. 29, 2018; U.S. patent application Ser. No. 13/952,564, entitled "WIDE DYNAMIC RANGE USING MONOCHROMATIC SENSOR," FILED Jul. 26, 2013; U.S. patent application Ser. No. 14/214,311, entitled "SUPER RESOLUTION AND COLOR MOTION ARTIFACT CORRECTION IN A PULSED COLOR IMAGING SYSTEM," filed Mar. 14, 2014; U.S. patent application Ser. No. 13/952,550, entitled "CAMERA SYSTEM WITH MINIMAL AREA MONOLITHIC CMOS IMAGE SENSOR," filed Jul. 26, 2013, each of which is incorporated herein by reference in its entirety. Doppler wavelength shifting may be used to identify the number, size, speed, and/or directionality of moving particles, for example. Doppler wavelength shifting may be used with multiple laser wavelengths to interrelate the tissue depth and moving particles, for example. Tissue refractivity may be used for identification of irregular or variability of tissue superficial and subsurface aspects, for example. In surgical practice, it may benefit identifying tumor margins, infection, broken surface tissue, adhesions, changes in tissue composition, and the like. NIR Fluorescence may include techniques in which systemically-injected drugs are preferentially absorbed by targeted tissue. When illuminated with the appropriate wavelength of light, they fluoresce and can be imaged through a NIR-capable scope/camera. Hyperspectral imaging and/or multispectral imaging may include the illumination and assessment of tissue across many wavelengths throughout the electromagnetic spectrum to provide real-time images. It may be used to differentiate between target tissues. It may also enable an imaging depth of 0-10 mm for example. Confocal laser endomicroscopy (CLE) may uses light to capture high-resolution, cellular level resolution without penetrating into tissue. It may provide a real-time histopathology of tissue. Technology that uses light to capture micrometer-resolution, 3D images from within tissues. Optical coherence tomography (OC) may employ NIR light. OCT may enable imaging of tissue at depths of 1-2 mm, for example. Raman spectroscopy may include techniques that measure photon shifts caused by monochromatic laser illumination of tissue. It may be used to identify certain molecules. Photoacoustic imaging may include subjecting tissue to laser pulses such that a portion of the energy causes thermoelastic expansion and ultrasonic emission. These resulting ultrasonic waves may be detected and analyzed to form images.

The laser-light illumination source 10010 may include any illumination source of laser light suitable for analyzing human tissue. The laser-light illumination source 10010 may include a device such as the source laser emitters. The laser light illumination source 10010 may use one or more wavelengths of laser light to illuminate the tissue 10002. For example, the laser-light illumination source 10010 may use a red-blue-green-ultraviolet 1-ultraviolet 2-infrared combination. This combination with a 360-480 Hz sampling and actuation rate, for example, would allow for each light source to have multiple frames at an end user 60 Hz combined frame rate. A laser light wavelength combination with independent sources may increase resolution from a single array and may enable various depth penetration.

The tissue 10002 may be human tissue within a portion of a surgical field, for example. The laser light may reflect from the tissue 10002, resulting in reflected laser light. The reflected laser light may be received by the light sensor 10012. The light sensor 10012 may be configured to receive reflected laser light from a least a portion of the surgical field. The light sensor 10012 may be configured to receive laser light from the entirety of the surgical field. The light sensor may be configured to receive reflected laser light from a selectable portion of the surgical field. For example, a user, such as a surgeon, may direct the light sensor and the light laser light illumination source and/or the laser light illumination source to analyze specific portions of the surgical field.

The light sensor 10012 may be any device suitable for sensing reflected laser light and outputting corresponding information. For example, the light sensor 10012 may detect one or more characteristics of the reflected laser light, such as amplitude, frequency, wavelength, doppler shift, and/or other time domain or frequency domain qualities, for example. The laser-light sensor 10012 source may include a device such as the light sensor disclosed in connection with FIGS. 9A-C for example.

The laser-light sensor 10012 may include one or more sensor modules 10013. The sensor modules 10013 may be configured to measure a wide range of wavelengths. The sensor modules 10013 may be tuned and/or filtered to measure specific wavelengths for example. The sensor modules 10013 may include discrete sensors, a collection of sensors, a sensor array, a combination of sensor arrays, or the like, for example. For example, the sensor modules 10013 may include semiconductor components such as photodiodes, CMOS (complementary metal oxide semiconductor) image sensors, CCD (charge coupled device) image sensors, or the like. The laser-light sensor 10012 may include a dual CMOS arrays. Details on using FPGA in imaging system can be found in U.S. patent application Ser. No. 17/062,521, entitled TIERED-ACCESS SURGICAL VISUALIZATION SYSTEM, filed Oct. 2, 2020, which is herein incorporated by reference in its entirety.

Figure 15:
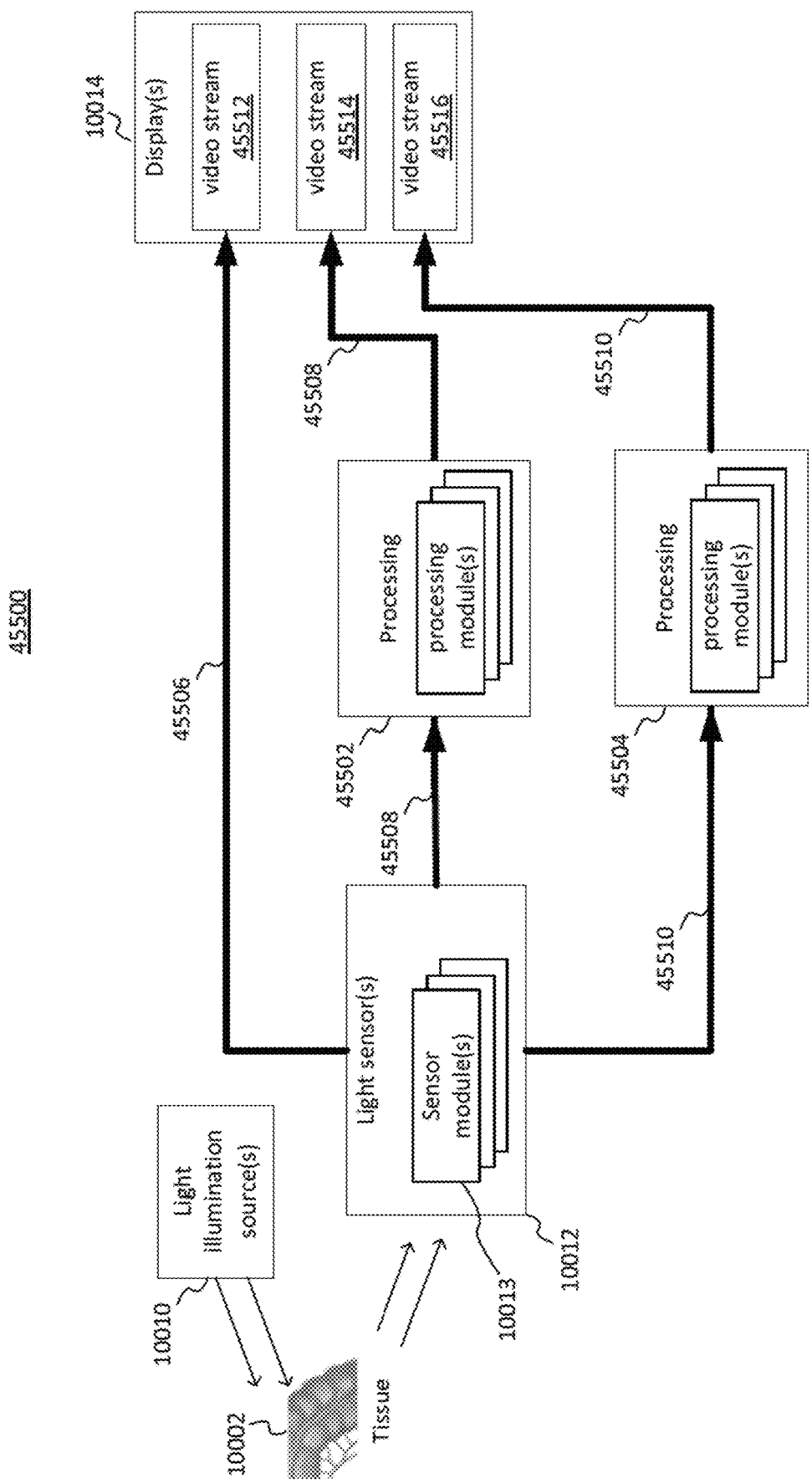
FIG. 15 illustrates an example visualization system.

FIG. 15 illustrates an example aspect of the visualization system described herein. Example surgical visualization system 45500 may be used to analyze tissue 10002 within the at least a portion of the surgical field. The surgical visualization system 45500 may include laser-light illumination source(s) 10010, light sensor(s) 10012, display(s) 10014, and/or one or more processing units 45502 and 45504. The surgical visualization system 45500 may include components and functionality described in connection with FIG. 14 for example, such as laser-light illumination source(s) 10010, light sensor(s) 10012 including sensor module(s) 10013, and/or display(s) 10014. The surgical visualization system 45500 may include components and functionality described in connection with FIGS. 9A-C for example.

As shown in FIG. 15, one or more surgical video streams generated from light sensors(s) 10012 may be transmitted via pathway 45506, pathway 45508, pathway 45510 and/or other pathways to display(s) 10014. The surgical video streams may include various video feeds described herein with reference to FIGS. 9-14. The surgical video streams may include a primary visual video feed, such as an intra-body camera feed. The surgical video streams may include one or more secondary surgical video feeds such as video streams associated with multispectral analysis, video streams associated with Doppler flowmetry, video streams of different spectral ranges, video streams captured using visible light and light outside of the visible range, video streams captured at different time intervals, and/or video stream(s) for overlaying onto another video stream.

The surgical video stream(s) may be processed via one or more processing modules. For example, video stream 45514 may be processed via a processing module(s) 45502, and the video stream 45516 may be processed via processing module(s) 45504. The video streams may be multiple feeds of the same source stream being communicated and processed separately. As shown, video stream 45512 may be transmitted via a dedicated communication pipeline, bypassing processing modules, such as processing modules 45502 and 45504. For example, video stream 45512 may be an HD video feed with no processing or intermediate steps between scope and display. The video streams 45514 and 45516 may be sent through post capture processing to extract or convert the video or image(s) to supply other visualization capabilities. Video stream 45512 may be the same as the video streams 45514 and/or 45516 prior to processing via processing module(s) 45502 and/or 45504. Processing 45502 and 45504 can be the same or different.

As shown in FIG. 15, redundant surgical imaging communication pipe ways and processing may provide a fail-safe condition for the primary visual light feed. The primary video stream may be transmitted via multiple pathways. For example, the video stream may be divided into different portions for transmission via multiple pathways. A portion of the video stream, for example, every other picture frame, may be transmitted via a pathway, and the rest of the video stream or the remaining picture frames may be transmitted via another pathway. The two portions may be combined or merged prior to display. Thus, transmission speed of the video feed may be increased and may overcome the data storage and transport limits of the system architecture. For example, the two video stream portions may be encoded such that they may be independently decoded and displayed without being re-combined. Combining the two portions may result in a higher quality video feed; however, displaying a video stream portion may provide sufficient view of the surgical site for a surgeon. If an issue associated with a pathway for transmitting a portion of the video stream is detected, combining or merging of the video stream portions may be suspended, and the video stream portion that has successfully been transmitted to the display system may be displayed.

The primary video stream may be processed via multiple instances of the same processing module(s) through different pathways. If an instance of the processing modules experience latency or failure, the video stream may be processed via another instance of the processing modules may be displayed. If processing causes undue latency or experiences failure, the video stream that bypasses processing may be displayed. Utilizing multiple video stream paths may improve processing speed and reliability, as an individual pathway may be associated with isolated individual processing elements. By performing processing tasks in parallel, the failure of one video feed may not result in the loss of all feeds. Performing different processing tasks in parallel and combine the processed video streams for display may increase processing throughput and reduce latency.

For example, the computing system may control the capturing, processing, and/or communication of the visualization feed(s) to prioritize latency over reliability, or prioritize reliability over latency. The priority focus may be controlled or updated dynamically. For example, the computing system may prioritize within the FPGAs such that latency may be reduced. The visualization feed(s) may be prioritized within the FPGAs such that the reliability of the video stream may be improved. For example, the computing system may adjust the communication paths such as communication paths 45506, 45508 and 45510 to prioritize latency over reliability, or prioritize reliability over latency. For example, allocating more communication pathways to transmit the same video stream may increase reliability, and allocating communication pathways for parallel processing may reduce latency.

Thus, the redundancy allows for the advanced computational imaging processing, reduced latency, and/or allow a communication to fail while still providing an assured visual feed of the camera.

Figures 16, 17:
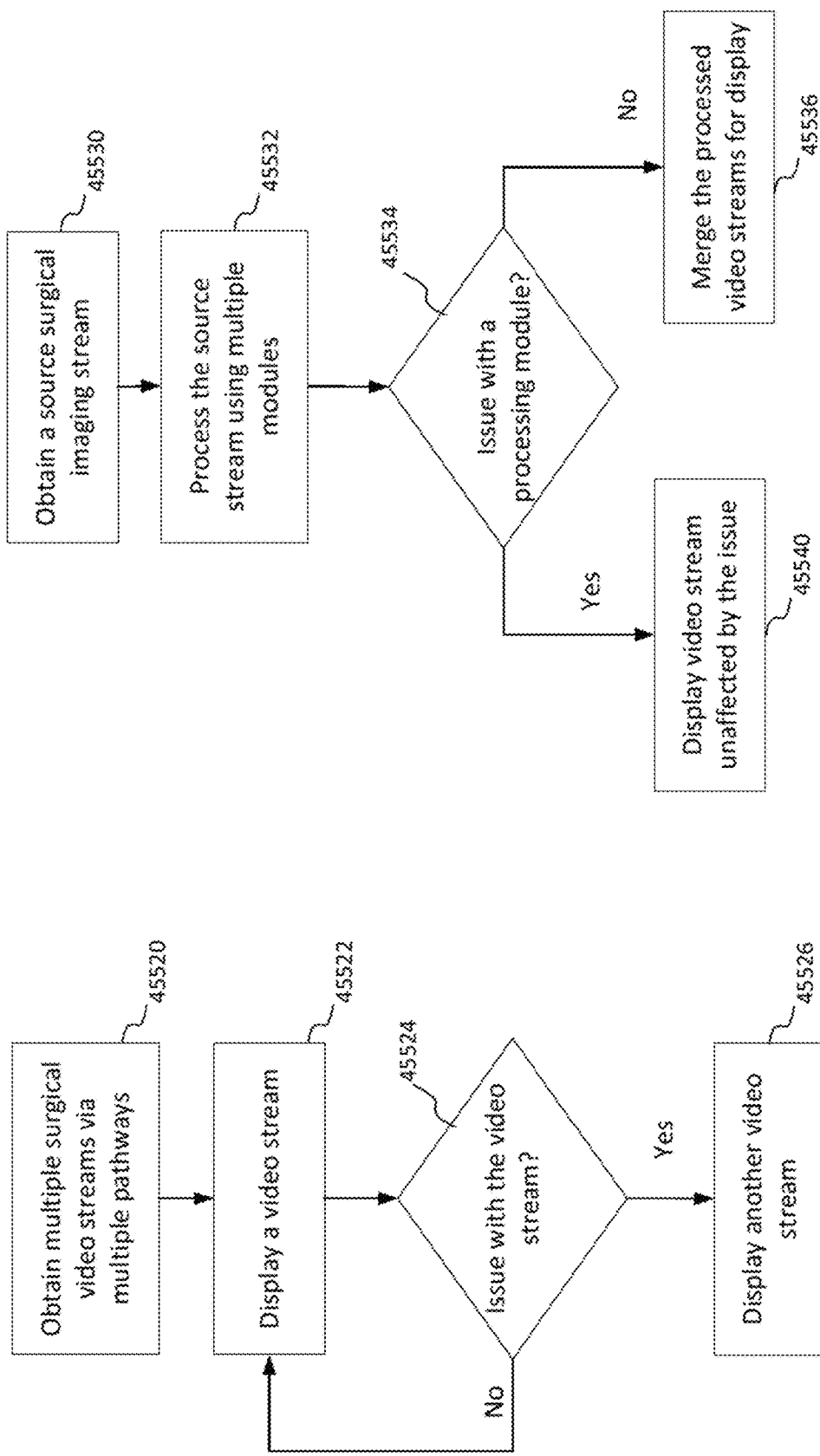
FIG. 16 illustrates an example process for using redundant pipe ways for communicating surgical imaging feed(s).
FIG. 17 illustrates an example process for using redundant processing paths for communicating surgical imaging feed(s).

FIG. 16 illustrates example process for using redundant pipe ways for communicating surgical imaging feed(s). At 45520, multiple surgical video streams may be obtained via multiple pathways. The multiple video or imaging feeds could be copies of the same feed with different pathways to the user display. For example, a first video stream may be obtained via a communication pathway, and a second video stream may be obtained via another communication pathway. The multiple surgical video streams could be bifurcated allowing a portion of the feed to pass down one path and a different portion to pass through another pathway. For example, a surgical video stream may be an HD video feed, and a surgical video stream may be of a higher quality video stream or a video stream with added visualization capabilities. The multiple surgical video streams may be obtained from the same intra-body visual light feed, or may be obtained from different intra-body visual light feeds. At 45522, a video stream may be displayed. At 45524, whether the video stream being displayed has encountered at least one issue may be determined. Upon detecting an issue with the video stream being displayed, at 45526, another video stream may be displayed. For example, the primary video stream may be displayed initially. Upon detecting an issue associated with the primary video, the secondary video stream may be displayed. The redundant communication pathways may be used in parallel to improve reliability, communication speed, throughput, and/or to reduce latency of surgical imaging/video feeds for display.

FIG. 17 illustrates example process for using redundant processing paths for processing surgical imaging feed(s). At 45530, a source surgical imaging stream may be obtained. For example, the source surgical imaging stream may be obtained as described herein with reference to FIGS. 9-15. At 45532, the source stream may be processed using multiple processing modules. For example, at least some processing modules may be used to process the surgical imaging stream in parallel. At 45534, whether an issue has been encountered at a processing module may be determined. If no issue has been found, the processed video streams may be merged for display at 45536. Upon detecting an issue associated with a processing module, at 45540, a video stream unaffected by the detected issue may be displayed. For example, a video stream that has not been processed by the processing module associated with the detected issue may be selected for display.

For example, surgical imaging stream generated from light sensors(s) 10012 as shown in FIG. 15 may be obtained. The source surgical imaging stream may be processed using processing module(s) 45502 and processing module(s) 45504 in parallel. The processing module(s) 45502 and the processing module(s) 45504 may be different instances of the same type of processing modules. The processed video stream 45514 and the processed video stream 45516 may be merged for display.

Upon detecting an issue associated with processing module(s) 45504, the processed video stream 45516 may become unavailable, and merging of the processed video streams 45514 and 45516 may be stopped. The processed video stream 45514 may identified as a video stream unaffected by the detected issue and may be displayed. The video stream 45512 shown in FIG. 15, which bypasses the processing modules, may be identified as a video stream unaffected by the detected issue and may be displayed. For example, the unprocessed video stream may be selected for display when both processing module(s) 45502 and 45504 encounter issues. For example, the computing system may detect an issue associated with a processing module and provide an indication of the processing interruption. The computing system may provide an option to an HCP to enable the HCP to manually control the visualization system. The computing system may allow the user to select bypassing processing aspects of the visualization system. Thus, computing system may ensure that the user can display the video even if the hardware processing fails. The processing module(s) 45502 and the processing module(s) 45504 may be used in parallel to improve processing throughput, reduce latency, and/or to guarantee the availability of surgical imaging stream for display.

For example, a source video stream, such as a video stream generated from light sensors(s) 10012 as shown in FIG. 15 may be divided into different portions to be processed separately. A portion of the video stream, for example, every other picture frame, may be processed using a first processing module such as processing module(s) 45502, and the rest of the video stream or the remaining picture frames may be processed using a second processing module such as processing module(s) 45504. The two processed video portions, such as processed video streams 45514 and 45516 may be combined or merged prior to display. Thus, processing speed of the video feed may be increased and may overcome the processing limits of the system architecture. Combining the two portions may result in a higher quality video feed; however, displaying a video stream portion may provide sufficient view of the surgical site for a surgeon. If an issue associated with a processing module is detected, combining or merging of the video stream portions may be suspended, and the video stream portion that has successfully been processed may be displayed.

For example, multiple source video streams may be generated from light sensors(s) 10012 as shown in FIG. 15. The source video streams may contain images associated with different temporal aspects. The video streams, for example, after processing, may be merged for display. The video streams may be displayed on their own, without merging. For example, a video stream may serve as a redundant backup supply to ensure the user has display of the source despite of an issue with a processing module or a communication pathway.

Example processing modules may include, but not limited to, multispectral analysis module as described herein with reference to FIG. 14, Laser Doppler flowmetry analysis module as described herein with reference to FIGS. 12 and 13, field programmable arrays, a content composite module, and/or the like.

An example processing module may be configured to enhance a surgical video stream using another video stream. For example, the computing system may derive contextual information associated with the surgery by analyzing a video stream described herein. The contextual information may be used to enhance another surgical video stream. For example, the computing system may extract one or more portions (e.g., a portion that includes an area of interest) from a surgical video stream and overlay the extracted portion onto another surgical video stream, as described herein.

An example processing module may be configured to annotate the surgical video. As those skilled in the art may appreciate, a video may be annotated with metadata. Visual annotation may include denoting locations of object or people of interest in the video, describing objects in the video, describing the context of the scene, and/or providing other information. For example, the processing module may be configured to annotate the microsurgical outcomes. The processing module may be configured to analyze the video feed and identify the point(s) in time to add label(s). The processing module may receive data from surgical device(s) and may be configured to annotate data captured via device sensor(s), such as raw sensor data. The processing module may be configured to annotate scaling. The processing module may be configured to convert the video stream for use with a 3D environmental visualization tool. The annotations may be inserted on time stamp or on the video itself. The processing module may receive input from HCPs, such as resident diaries. The raw sensor data may be coupled with resident diaries when annotated into the surgical video. The video stream for use with a 3D environmental visualization tool may be annotated with resident diaries. The processing module may be configured to track an object of interest and identify the object's contour when it is obstructed or partially obstructed. The processing module may annotate the contour of the object of interest in the video. The processing module may receive surgical information such as contextual information from the situationally aware surgical hub as described herein with reference to FIG. 8 and may insert the contextual information into the video. The processing module may be configured to annotate of a process of multiple events through time.

An example processing module may be configured to derive contextual information associated with a surgery by analyzing a video stream described herein. The derived contextual information may be indicated in (e.g., inserted into) another video stream. For example, as described herein, the derived contextual information may be inserted into an overlay region described herein.

Objects may be recognized and tracked via video processing from video captured by one or more imaging systems. The video may be analyzed to identify objects. For example, a processing module may identify and highlight known objects via annotation, such that the recognized object may be recognizable with frame-to-frame outlining.

The processing module may localize one or more objects of interest in the video. For example, the processing module may predict an object in an image within a boundary. Various known image or video processing technologies, such as keypoint detection and analysis, bounding box annotation, polygon mesh processing, image segmentation, facial recognition, gesture recognition, point cloud, lines and splines, and/or the like may be used to analyze the video feeds. Those skilled in the art may appreciate that various object detection and tracking technologies used in autonomous vehicle may be used in surgical video processing.

The video may be processed to identify the motion of HCP(s) and/or object(s). Based on the motion information, the surgical activities and/or actions of the HCP(s) may be determined. For example, the HCPs or objects may be tracked and categorized based on motion, function, and/or manipulation. Repeatable pattern of events may be identified.

Video may be stored during processing, as a part of the display of the video. The computing system may be configured to erase the video after processing and transferring the video, to address privacy concerns and retention aspects of in-process video.

A computing system may generate a composite video stream from multiple input feeds. The computing system may obtain a surgical video stream and overlay content associated with a surgical procedure. The computing system may determine the overlay region location for overlaying the overlay content by analyzing the content of surgical video stream. For example, based on the content of a frame of the surgical video stream, the computing system may determine an overlay region location in the frame for overlaying the overlay content; based on the content of a subsequent frame of the surgical video stream, the computing system may determine another overlay region location in the subsequent frame for overlaying the overlay content. The composite video stream may be generated based on the overlay region locations determined for different frames of the surgical video stream.

For example, the surgical video stream may be a video feed of the surgical site from a laparoscopic scope, and the composite video stream may be generated by overlaying the overlay content onto the video of the surgical site at the determined overlay region location. The location, orientation, and/or size of the overlay content may be adjusted on the surgical site in the video stream as the laparoscopic scope moves. The surgical video stream may include frames having a surgical instrument, and the composite video stream may be generated by overlaying the overlay content onto the surgical instrument at the determined overlay region location. The location, orientation, and/or size of the overlay content may be adjusted in the video stream as the surgical instrument moves.

For example, the primary imaging of the surgical site may be supplemented by overlaying or inserting secondary video feed(s) and/or data overlays. The overlay content may adjust as the primary scope image moves and may be oriented with respect to the surgical site and the surgical instrument(s). The overlay content may cover the entire primary imaging or may cover a portion of the primary imaging feed. The overlay region may coincide with a predefined location on an instrument based on one or more fiducial marker(s) on the instrument.

FIG. 18 illustrates an example process for generating a composite surgical video stream from multiple input feeds. At 45550, a surgical video stream may be obtained. For example, the computing system may obtain the surgical video stream via an imaging device such as the imaging device 20030 described herein with respect to FIG. 2. For example, the computing system may obtain the surgical video stream as described herein with reference to FIGS. 9-15. The surgical video stream may be or may include a video feed of the surgical site from a laparoscopic scope. For example, the computing system may obtain the surgical video stream via one or more cameras in the OR, such as cameras 20021 as described herein with reference to FIG. 2.

At 45552, overlay content may be obtained. Overlay content may include information associated with a device such as a surgical instrument. For example, overlay content for overlaying onto an energy device in an image or video may include an indication of the energy blade temperature, an indication of the energized state (e.g., due to capacitive coupling), and/or other information associated with the energy device. For example, the overlay content may include steps-for-use instructions associated with a surgical instrument.

For example, overlay content for overlaying onto a surgical stapling and cutting device the in an image or video may include an indication of the loading condition of the surgical instrument (e.g., whether a cartridge is loaded). The loading condition on the surgical instrument may be sensed, and the overlay content may be generated based on the sensed loading condition. This may prevent a knife blade from moving forward when cartridge is not loaded, or improperly loaded.

The overlay content can include a label for the anatomical section and a peripheral margin of at least a portion of the anatomical section. The peripheral margin can be configured to guide a surgeon to a cutting location relative to the anatomical section. The overlay content may include a supplementary image of an organ associated with the surgical procedure. The overlay content may include alternative imaging. The overlay content may include one or more of data obtained via pre-surgery tumor MRI, CT imaging, relevant pre-surgery data, ICG data, real-time doppler monitoring, procedural steps, device status, and/or other overlays customizable by the users. The overlay content may include an indication associated with previous procedure steps of the surgery, such as previous stapling(s) and/or previous weld(s).

Overlay content may include a secondary video feed or a portion of a secondary video feed. For example, the secondary video feed may be a video feed that has been processed via one or more processing modules as described herein with respect to FIG. 15. The secondary video feed may be a video associated with the current surgical procedure. The secondary video feed may be a tutorial video showing how to carry out the procedural steps. The secondary video feed may be a surgical simulation video. The secondary video feed may be a video of previous procedure steps. For example, the secondary video feed may be a video of previous stapling(s) and/or previous weld(s). This may enable the HCP to compare previous work with the current procedural step, for example, to identify the transection site more readily. The computing system may extract a portion of the secondary surgical video feed as the overlay content. For example, the portion of the secondary surgical video that includes a region of interest may be identified and extracted.

For example, the overlay content may be obtained from another video feed, a surgical hub described herein, from one or more surgical devices described herein, and/or from one or more sensors described herein. The overlay content may be updated in real time, in response to a change in a location and/or orientation of the surgical instrument within the surgical instrument frame. Various overlay content and obtaining the overlay content is further described in U.S. patent application Ser. No. 17/062,509 titled INTERACTIVE INFORMATION OVERLAY ON MULTIPLE SURGICAL DISPLAYS, filed Oct. 2, 2020, which is incorporated by reference herein in its entirety.

At 45554, the location, size and/or orientation of the overlay region may be determined. The computing system may determine the overlay region location for overlaying the overlay content by analyzing the content of surgical video stream. In examples, in-image markings may be used for insertion of data, images, and alternative imaging streams. By tracking and reading markers on instrument, the computing system may overlay information at a consistent location relative to the instrument such that the overlay content may move as the instrument moves in the video feed.

One or more overlay region(s) may be determined based on one or more fiducial marker(s). For example, a surgical instrument, such as the surgical instrument described herein with reference to FIG. 7, may include one or more fiducial markers. The fiducial markers may be placed at predetermined location(s) on the surgical instrument. The locations for placing fiducial markers may include an area on the surgical instrument suitable for overlaying overlay content. The locations for placing fiducial markers may include an area suitable for gauging the orientation of the surgical instrument and/or the distance of the instrument to the imaging system (e.g., a camera). The fiducial markers may be visible or invisible to human eyes, but recognizable via video processing. The fiducial markers may be of specific shapes, such that the computing system may identify the surgical instrument based on the fiducial marker(s).

The fiducial markers may be in a predefined pattern such that the computing system may identify the surgical instrument based on the fiducial marker. For example, the fiducial marker may include an electronic-readable code, such as QR code. The computing system may obtain a video feed that captures the fiducial marker and identify the surgical instrument based on the electronic-readable code (e.g., captured in a video feed or imaging feed). Based on the electronic-readable code, the computing system may retrieve information associated with the surgical instrument, such as the model of the surgical instrument. For example, using the electronic-readable code, the computing system may obtain the spatial property information associated with the fiducial marker(s) on the surgical instrument. The computing system may scale the overlay content based on the obtain spatial property of the marker(s) and the marker(s) in the video/imaging feed.

The size of the overlay region may be determined based on the size of an area on the surgical instrument suitable for content overlay, the size of a fiducial marker in real life, and the size of the fiducial marker in a video frame of the surgical video stream (e.g., a ratio between the real-life size and the imaged size). For example, the computing system may identify the fiducial marker in the video frames of the surgical video stream and determine the respective location, size, and/or orientation of the fiducial marker(s) in respective video frames. For a given video frame, or a group of video frames, the computing system may determine the size, location and/or orientation of the overlay region based on the location, size and/or orientation of the fiducial marker captured therein.

Details on fiducial markers and spatial awareness of surgical products and instruments can be found in application entitled HUB IDENTIFICATION AND TRACKING OF OBJECTS AND PERSONNEL WITHIN THE OR TO OVERLAY DATA THAT IS CUSTOM TO THE USER'S NEED, Ser. No. 17/384,508, filed contemporaneously, the contents of which are incorporated by reference herein.

As described herein, the overlay content may include an indication of previous stapling(s) or previous weld(s). The overlay content may include alternative imaging such as CT image indicating the tumor. The overlay region may be determined such that the overlay content may be inserted next to but not interfering with the current jaw placements. This may enable the user to compare previous work with the current and/or view the alternative imaging within the jaws to identify the tumor and/or transection site more readily.

At 45556, a composite video stream may be generated by overlaying the overlay content onto the surgical video stream. A composite video stream may be generated, for example, by inserting the overlay content into the surgical video stream, such as a primary surgical video feed. For example, overlay content may be scaled, oriented and inserted onto the shaft of a surgical instrument, based on the fiducial marker(s) captured in the primary video. The location, size, shape and/or orientation of the overlay region may be adjusted dynamically, for example, as the surgical device of interest moves in the primary video. For example, when the overlay content includes a secondary video feed or a portion of a secondary video feed, the composite video may be generated using "picture-in-picture" techniques. The computing system may determine a first overlay region size for overlaying the overlay content onto the first surgical video frame based on content of the first frame, and a second overlay region size for overlaying the overlay content onto a second surgical overlay frame based on content of the second frame. The computing system may scale the secondary surgical video stream, or a portion of the secondary video stream that contains the region of interest based on the determined first overlay region size and the determined second overlay region size.

FIG. 18B shows an example process for generating a composite surgical video stream using a fiducial marker. At 45553, a surgical video stream may be obtained, for example, as described herein. At 45555, a fiducial marker may be identified in a video frame of the surgical video stream. At 45557, the overlay region location, orientation and/or size may be identified for inserting overlay content into the video frame. At 45559, the overlay content may be inserted into the overlay region. The process may be repeated for each frame, every other frame, every n frames, periodically, or aperiodically. For the example, the overlay region location, orientation and/or size may be updated upon determining that the content of the primary stream changes (e.g., the location of the surgical instrument changes significantly, the orientation of the surgical instrument changes significantly). For example, the fiducial marker may be placed on a surgical instrument. By identifying the fiducial marker in the video frames and using the identified fiducial marker to determine the overlay region, the overlay content may move in the composite video stream as the surgical instrument moves in the surgical video stream.

Figure 19A:
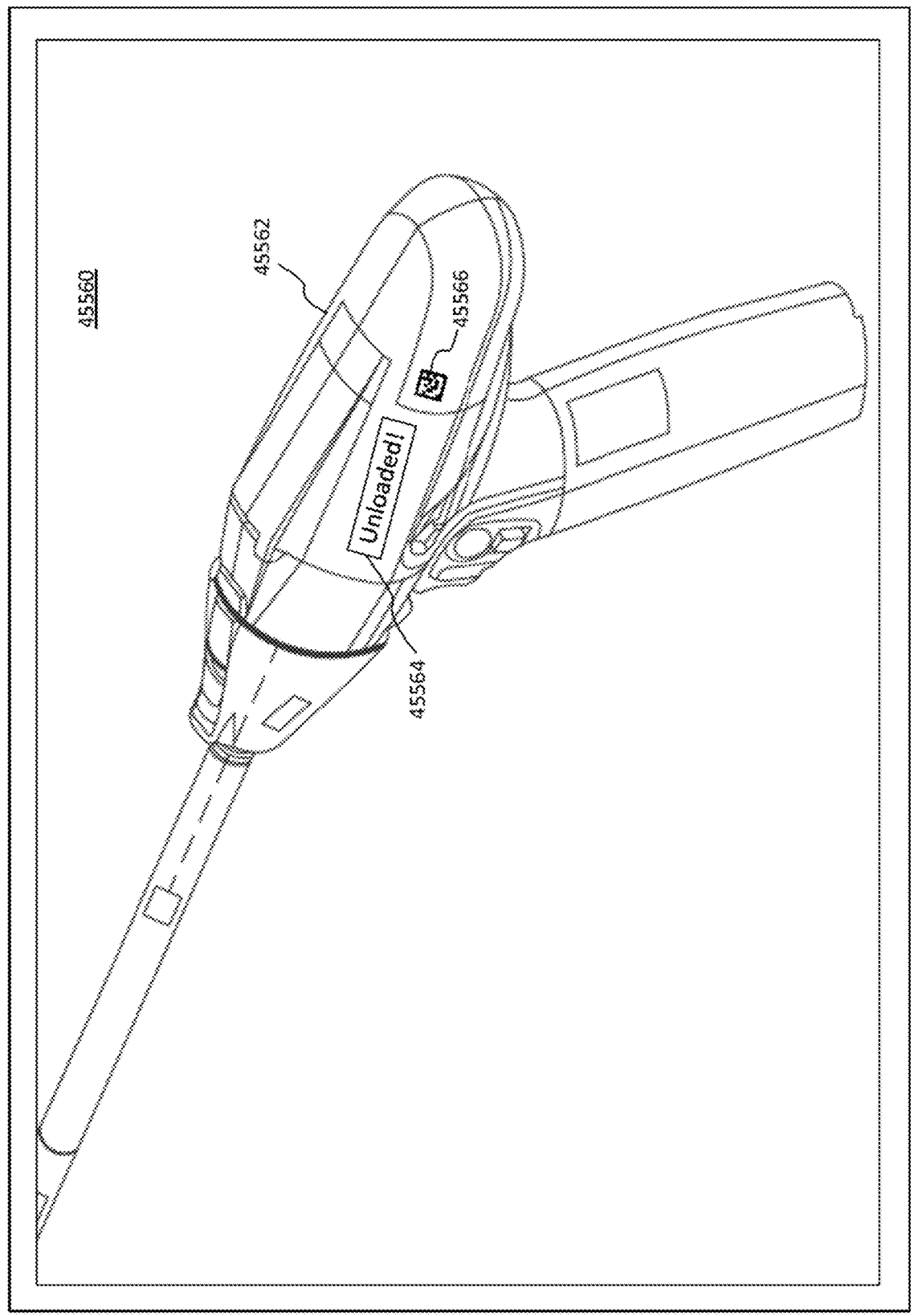
FIGS. 19A-19C illustrate example frames of a composite surgical video stream with overlay content that moves as a surgical instrument in the surgical video stream moves.
Figure 19B:
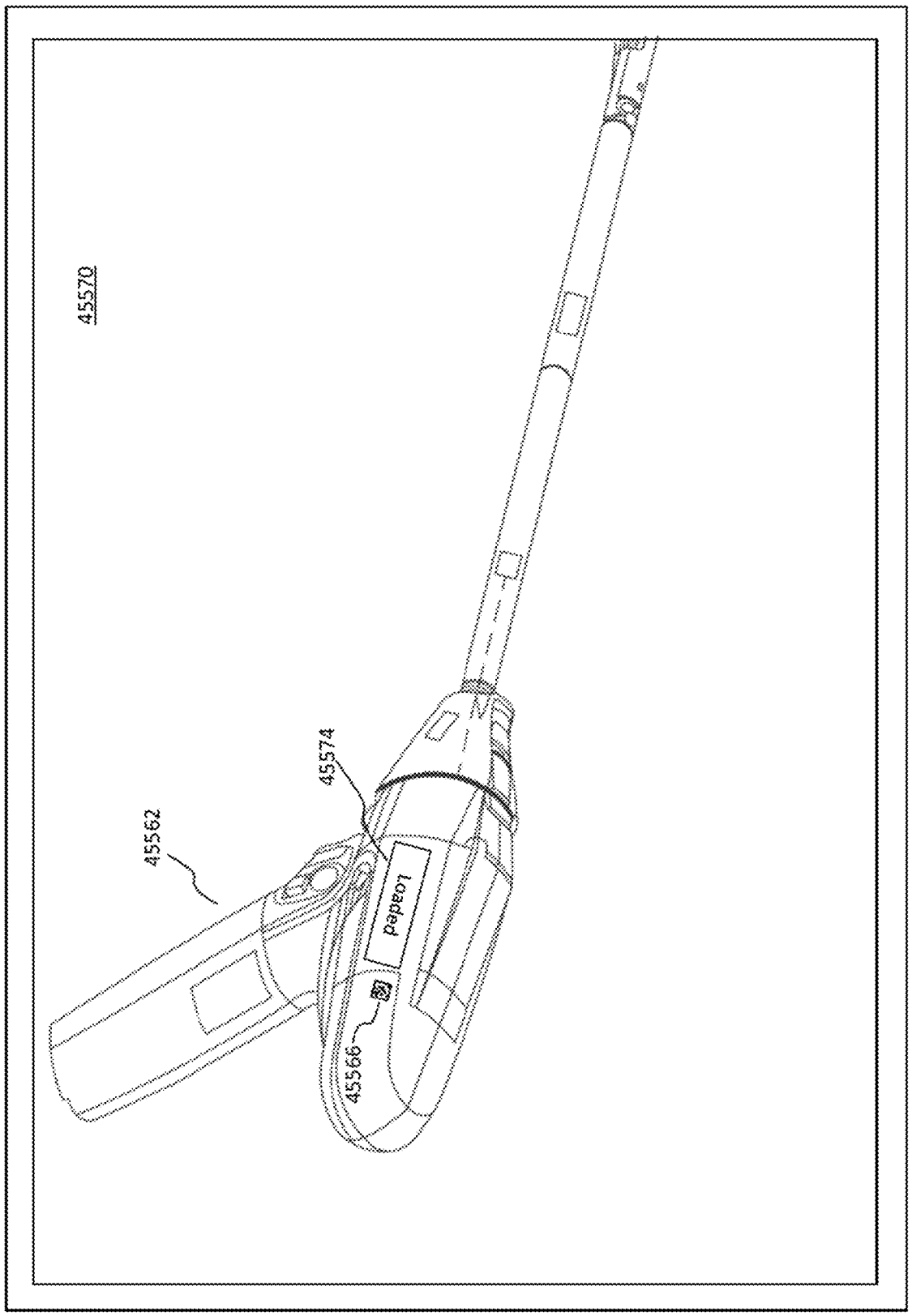
Figure 19C:
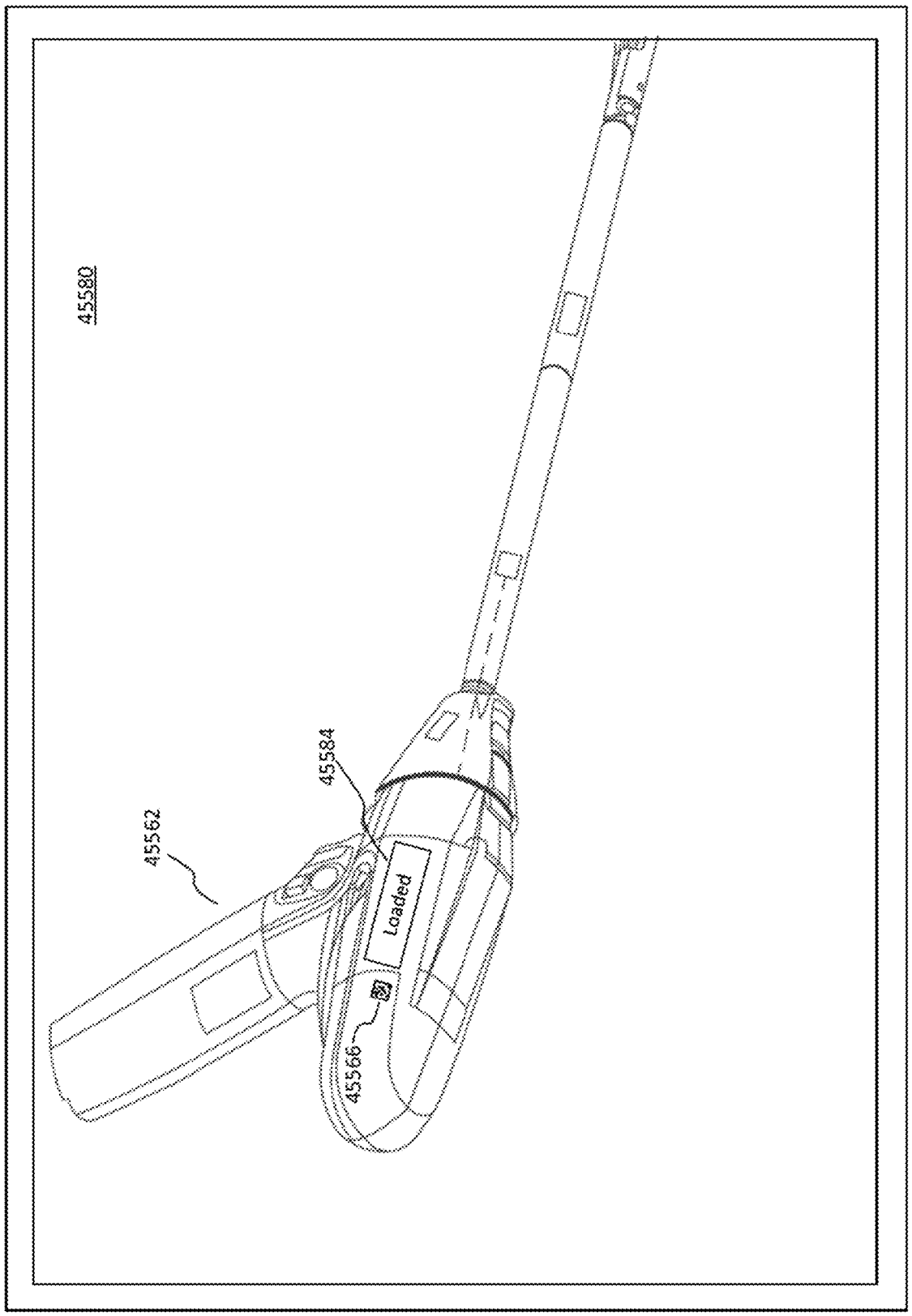

FIGS. 19A-C illustrate example video frames of a composite surgical video stream with overlay content that moves as a surgical instrument in the surgical video stream moves. As described herein, a composite surgical video stream may be generated by inserting overlay content into a surgical video feed at one or more determined overlay regions. The composite surgical video stream may include video frames with overlay content, which may be adjusted based on the content of corresponding frame from the surgical video feed.

FIG. 19A shows an example video frame 45560 of an example composite surgical video stream. As shown, video frame 45560 may include an image of a surgical instrument 45562, such as the surgical instrument 20282 described herein with respect to FIG. 7. The overlay content 45564 may indicate the loading condition of the surgical instrument 45562, such as "unloaded," as shown in FIG. 19A. The overlay region for inserting the overlay content 45564 may be determined based on the fiducial marker 45566 on the surgical instrument 45562.

For example, the computing system may identify the location, size and/or orientation of the fiducial marker 45566 in a primary video frame of the primary video feed. Based on the location, size and/or orientation of the fiducial marker 45566 in the primary video frame, the computing system may determine the location, size and/or orientation of the overlay region, as described herein. As shown in FIG. 19A, the overlay region may be identified such that the overlay content is easy to read and proportional to the surgical instrument.

FIG. 19B shows an example video frame 45570 of an example composite surgical video stream. As shown in FIG. 19B, the overlay content 45574 may reflect an updated loading condition of the surgical instrument 45562, "loaded." The surgical instrument 45562 and the fiducial marker 45566 shown in video frame 45570 have moved compared to surgical instrument 45562 and the fiducial marker 45566 shown in video frame 45560. Based on the location of the fiducial marker 45566, the computing device may determine the location of the overlay content region for overlay content 45574. The surgical instrument 45562 and the fiducial marker 45566 shown in video frame 45570 is smaller compared to surgical instrument 45562 and the fiducial marker 45566 shown in video frame 45560. Based on the size of the fiducial marker 45566, the computing device may determine the size of the overlay content region for overlay content 45574. As shown in FIG. 19B, the overlay content 45574 is scaled down from the overlay content 45564 shown in FIG. 19A. The surgical instrument 45562 and the fiducial marker 45566 shown in video frame 45570 is in an "upside down" orientation compared to surgical instrument 45562 shown in video frame 45560. Based on the orientation of the fiducial marker 45566, the computing device may determine the orientation of the overlay content region for overlay content 45574. As shown in FIG. 19B, the overlay content 45574 is upside down as well. FIG. 19C shown an example video frame 45580 of an example composite surgical video stream. As shown, the overlay content 45584 may be moved and scaled based on the fiducial marker 45566 but may be kept in upright or substantially upright orientation to improve readability.

For example, de-identification may be performed for the video feed(s) described therein. De-identification process may be performed at the edge computing system, described herein with reference to FIG. 1B. For example, faces captures in the video feed(s) may be detected and blurred by the computing system. Face, silhouette, gait, and/or other characteristics may be obscured. Other person-identifying content, such as ID badges, may be detected, blurred and/or removed from the video. In some instances, a laparoscopic video, which usually contains in-body imaging may accidentally include out-of-body images. Such images may be detected by the computing system may be removed from the video.

For example, video(s) obtained via in-room cameras may be correlated with video(s) obtained via in-body cameras to identify procedural progression information. The computing system may determine the surgical task being carried out based on the video frames obtained via intra-body scope in conjunction with the video frames obtained via OR qjcamera(s). The determination may be further based on one or more monitoring sensors described herein with reference to FIGS. 1-8. The computing system may identify an HCP (e.g., the HCP's role, present and/or pending task, and/or profession) based on the video frames obtained via intra-body scope and the video frames obtained via OR camera(s). Based on the determined procedural progression information and the identification of the HCP, the computing system may generate customized overlay content for the HCP. For example, the customized overlay content may be displayed via an augmented reality (AR) or mixed reality overlay on a user interface. The AR device may provide AR content to the HCP. For example, a visual AR device, such as safety glasses with an AR display, AR goggles, or head-mounted display (HMD), may include a graphics processor for rendering 2D or 3D video and/imaging for display. Based on the determined procedural progression information and the identification of the HCP, the computing system may generate a customized control signal to an equipment or a surgical device. For example, based on a determination that the HCP carrying an energy device is a nurse, the computing system may generate a control signal to prevent the energy device from entering the energized state. For example, based on a determination that the HCP carrying an energy device is a surgeon, the computing system may generate a control signal to allow the energy device to enter an energized state.

For example, 3D modeling may be performed by combining imaging video(s), pre-surgical imaging, and/or intra-operative imaging. For example, the computing system may analyze video frames of a primary surgical imaging or video feed to identify missing information for the primary surgical imaging or video feed. The computing system may identify region(s) of poor quality (e.g., artifacts, blurry, obstructed view, etc.) and may provide an indication to request additional imaging to supplement the primary surgical video feed.

The computing system may identify region(s) associated with incomplete or missing information in the surgical imaging or video feed based on the clarity of the region(s). The computing system may generate a notification indicating the identified region(s) associated with incomplete or missing information. For example, the notification may include an indication of the surgical imaging or video frame with the identified regions highlighted in a rendered shape and color. The computing system may interpolate the likely location and shape of the organ in the imaging or video frame.

The computing system may identify region(s) associated with potentially misleading data in the surgical imaging or video feed based on the clarity of the region(s). For example, region(s) with artifacts or defects exceeding a threshold value may be identified. The computing system may generate a notification indicating that the surgical imaging or video feed contains potentially misleading information. For example, the notification may include an indication of the surgical imaging or video frame with the identified regions marked as containing potentially misleading information.

The computing system may generate an indication with instructional information such as steps-for-use of what regions of the patient have inconclusive or insufficient imaging. The computing system may indicate information associated with access port(s) for input of the additional scan(s). The supplemental scan may be a different type of imaging/scanning from the primary image source. For example, a CT scan of the abdomen could have insufficient or inconclusive data for the inside of the liver, pancreas, or other solid organ. The computing system may provide an indication or notification of a means for scanning with an ultrasound imaging system. The computing system may obtain the imaging data from the supplemental scan and may combine the imaging data obtained from the primary imaging source with the imaging data obtained from the supplemental scan.

The computing system may fuse imagining data or videos obtained from different sources based on common anatomic landmarks. For example, the computing system may use the primary imaging as a source map for the supplementary image. The computing system, by analyzing the primary imaging, may identify the locations of content boundaries or borders, where the imaging data obtained from different sources may merge. For example, the computing system may use a third imaging source, such as imaging obtained via a laparoscope to identify linkable aspects for fusing the primary and secondary imaging data. For example, the computing system may fuse the primary and seconding imaging data based on preset imaging fiducial markers.

After performing imaging data fusing, the computing system may determine a completeness level of organ imaging for one or more portion of the fused imaging. The completeness level for a portion of the fused imaging may indicate an estimated completeness and/or accuracy of that portion of the fused image. In examples, the imaging data (e.g., still and/or video imaging data) may be generated via different energy imaging technologies. The completeness level of fused organ imaging may be determined based on the different energy imaging technologies.

The computing system may generate composite imaging data based on partial imaging data from multiple imaging feeds. The multiple imaging feeds may be received simultaneously. The composite imaging data may be generated in real-time. For example, one or more portion of the composite imaging data may include visual light imaging, while other portion(s) of the compositing imaging may include alternative source imaging as described herein. The computing system may generate the composite imaging data by replacing a portion of imaging data from one imaging feed with a corresponding portion of the imaging data from another imaging feed. The computing system may overlay a portion of imaging data from one imaging feed onto a corresponding portion of the imaging data from another imaging feed. The computing system may highlight (e.g., transparent highlight) a portion of imaging data from one imaging feed based on a corresponding portion of the imaging data from another imaging feed.

For example, one or more portion of a surgical video stream may be defined for expanded imaging overlay. The portions for expanding imaging overlay may be pre-defined or determined based on a surgeon's input during a surgical procedure. The portion(s) for expanded imaging overlay may include, but not limited to, a transection site, or a dissection site. The expanded imaging may include visualization of critical structure(s), blood supplies surrounding the transection site or the dissection site. For example, CT imaging may be superimposed on a surgical video stream (e.g., in a semi-transparent fashion). The expanded imaging overlay may enable a surgeon to select a transection or dissection path without damaging critical structure(s) of the patient's organ. The expanded imaging overlay may enable a surgeon to differentiate the vascular tree supplies blood to a tumor from blood vessels that do not supply blood to the tumor, and identify the blood vessels to be severed. Details on overlaying content on a video feed of a surgical site is further described in U.S. patent application Ser. No. 17/062, 509 titled INTERACTIVE INFORMATION OVERLAY ON MULTIPLE SURGICAL DISPLAYS, filed Oct. 2, 2020), which is incorporated by reference herein in its entirety.

The invention claimed is:

1. A computing system comprising:
 a processor configured to:
 obtain a plurality of surgical video streams via a plurality of communication pathways during a surgical procedure;
 process a first surgical video stream of the plurality of surgical video streams using a first processing module, the first processing module configured to perform at least one of analysis, enhancement, or annotation;
 process a second surgical video stream of the plurality of surgical video streams using a second processing module;
 send the first surgical video stream of the plurality of surgical video streams for display, wherein the first surgical video stream is obtained via a first communication pathway;
 detect an issue associated with the first processing module; and
 based on a detection of the issue associated with the first processing module, send the second surgical video stream of the plurality of surgical video streams for display, wherein the second surgical video stream is obtained via a second communication pathway, the second communication pathway being different from the first communication pathway.

2. The computing system of claim 1, wherein the first surgical video stream and the second surgical video stream are obtained from a same intraoperative imaging feed.

3. The computing system of claim 1, wherein the first processing module comprises at least one of:
 a multispectral analysis module;
 a laser Doppler flowmetry analysis module;
 a plurality of field programmable arrays; or
 a content composite module.

4. The computing system of claim 1, wherein the first surgical video stream and the second surgical video stream are associated with imaging data captured via a same light sensing element and, the first surgical video stream and the second surgical video stream are processed via different processing modules.

5. The computing system of claim 1,
 wherein the plurality of surgical video streams comprises a third surgical video stream, and
 wherein the processor is further configured to enhance the first surgical video stream using the third surgical video stream prior to sending the first surgical video stream for display.

6. The computing system of claim 1, wherein the processor is further configured to:
 process the first surgical video stream using the first processing module;
 process the second surgical video stream using the second processing module;
 merge the processed first surgical video stream and the processed second surgical video stream; and
 upon detection of the issue associated with the first processing module, suspend merging to the processed first surgical video stream and the processed second surgical video stream.

7. The computing system of claim 1, wherein the plurality of surgical video streams comprises a third surgical video stream, and the processor is further configured to:
- extract surgery annotation data from the third surgical video stream; and
- insert the extracted surgery annotation data into the first surgical video stream prior to sending the first surgical video stream for display.

8. The computing system of claim 1, wherein the first surgical video stream and the second surgical video stream are obtained from a single intra-body visual light feed.

9. A method comprising:
- obtaining a plurality of surgical video streams via a plurality of communication pathways during a surgical procedure;
- processing a first surgical video stream of the plurality of surgical video streams using a first processing module, the first processing module configured to perform at least one of analysis, enhancement, or annotation;
- processing a second surgical video stream of the plurality of surgical video streams using a second processing module;
- sending the first surgical video stream of the plurality of surgical video streams for display, wherein the first surgical video stream is obtained via a first communication pathway;
- detecting an issue associated with the first processing module; and
- based on detecting the issue associated with the first processing module, sending the second surgical video stream of the plurality of surgical video streams for display, wherein the second surgical video stream is obtained via a second communication pathway, the second communication pathway being different from the first communication pathway.

10. The method of claim 9, wherein the first surgical video stream and the second surgical video stream are obtained from an intraoperative imaging feed.

11. The method of claim 9, wherein the first processing module comprises at least one of:
- a multispectral analysis module;
- a laser Doppler flowmetry analysis module;
- a plurality of field programmable arrays; or
- a content composite module.

12. The method of claim 9, wherein the first surgical video stream and the second surgical video stream are associated with imaging data captured via a same light sensing element and, the first surgical video stream and the second surgical video stream are processed via different processing modules.

13. The method of claim 9,
- wherein the plurality of surgical video streams comprises a third surgical video stream, and
- wherein the method further comprises enhancing the first surgical video stream using the third surgical video stream prior to sending the first surgical video stream for display.

14. The method of claim 9, further comprising:
- processing the first surgical video stream using the first processing module;
- processing the second surgical video stream using the second processing module; and
- merging the processed first surgical video stream and the processed second surgical video stream,
- upon detecting the issue associated with the first processing module, suspending merging the processed first surgical video stream and the processed second surgical video stream.

15. The method of claim 9,
- wherein the plurality of surgical video streams comprises a third surgical video stream, and
- the method further comprises:
- extracting surgery annotation data from the third surgical video stream; and
- inserting the extracted surgery annotation data into the first surgical video stream prior to sending the first surgical video stream for display.

16. The method of claim 9, wherein the first surgical video stream and the second surgical video stream are obtained from a single intra-body visual light feed.

\* \* \* \* \*